United States Patent
Bae et al.

(10) Patent No.: US 11,667,647 B2
(45) Date of Patent: Jun. 6, 2023

(54) DELAYED FLUORESCENT COMPOUND, AND ORGANIC LIGHT EMITTING DIODE AND ORGANIC LIGHT EMITTING DISPLAY DEVICE INCLUDING THE SAME

(71) Applicants: LG Display Co., Ltd., Seoul (KR); Soulbrain Co., Ltd., Seongnam-si (KR)

(72) Inventors: Suk-Young Bae, Paju-si (KR); Tae-Ryang Hong, Paju-si (KR); Jun-Yun Kim, Paju-si (KR); Jin-Hee Kim, Paju-si (KR); Ah-Rang Lee, Paju-si (KR)

(73) Assignees: LG Display Co., Ltd., Seoul (KR); Soulbrain Co., Ltd., Seongnam-si (KR)

( * ) Notice: Subject to any disclaimer, the term of this patent is extended or adjusted under 35 U.S.C. 154(b) by 589 days.

(21) Appl. No.: 16/712,159

(22) Filed: Dec. 12, 2019

(65) Prior Publication Data

US 2020/0207778 A1 Jul. 2, 2020

(30) Foreign Application Priority Data

Dec. 27, 2018 (KR) .................. 10-2018-0170831

(51) Int. Cl.
| | | |
|---|---|---|
| *C07D 491/10* | (2006.01) | |
| *C07D 491/107* | (2006.01) | |
| *C07D 495/10* | (2006.01) | |
| *H01L 51/00* | (2006.01) | |
| *H01L 51/50* | (2006.01) | |

(52) U.S. Cl.
CPC ....... *C07D 491/107* (2013.01); *C07D 495/10* (2013.01); *H01L 51/0054* (2013.01); *H01L 51/0067* (2013.01); *H01L 51/0072* (2013.01); *H01L 51/0073* (2013.01); *H01L 51/0074* (2013.01); *H01L 51/5004* (2013.01)

(58) Field of Classification Search
CPC .............. C07D 491/107; C07D 495/10; H01L 51/0054; H01L 51/0067; H01L 51/0072; H01L 51/0073; H01L 51/0074; H01L 51/5004; H01L 51/5012; H01L 51/0059; H01L 51/0071; H01L 51/50; H01L 51/5024; C09K 11/06; C09K 2211/1007; C09K 2211/1033; C09K 2211/1037; C09K 2211/1059; C09K 2211/1062; C09K 2211/1066
USPC ....................................................... 428/690
See application file for complete search history.

(56) References Cited

U.S. PATENT DOCUMENTS

| | | | | |
|---|---|---|---|---|
| 10,566,561 B2* | 2/2020 | Kim | ............. | H01L 51/0072 |
| 10,889,602 B2* | 1/2021 | Kim | ............. | H01L 51/0094 |
| 11,557,731 B2* | 1/2023 | Choi | ............. | H01L 51/0067 |
| 2016/0380205 A1* | 12/2016 | Adachi | ............. | C07D 265/38 544/102 |
| 2020/0052226 A1* | 2/2020 | Seo | ............. | H01L 51/0073 |
| 2020/0190122 A1* | 6/2020 | Bae | ............. | H01L 51/0074 |
| 2020/0212309 A1* | 7/2020 | Choi | ............. | C09K 11/06 |
| 2021/0119147 A1* | 4/2021 | Yoon | ............. | C07D 487/04 |
| 2022/0006023 A1* | 1/2022 | Hong | ............. | H01L 51/0071 |
| 2022/0077401 A1* | 3/2022 | Hong | ............. | H01L 51/0067 |

FOREIGN PATENT DOCUMENTS

| | | |
|---|---|---|
| CN | 106470997 A | 3/2017 |
| KR | 10-2014-0076522 A | 6/2014 |
| KR | 10-2015-0034612 A | 4/2015 |
| KR | 10-2017-0059910 A | 5/2017 |
| WO | 2016/021989 A1 | 2/2016 |

OTHER PUBLICATIONS

CAS reg. No. 2447639-36-1, Jul. 21, 2020. (Year: 2020).*
Office Action issued in corresponding Chinese Application No. 201911293769.6 dated Feb. 15, 2022.

* cited by examiner

*Primary Examiner* — Douglas J McGinty
(74) *Attorney, Agent, or Firm* — Morgan, Lewis & Bockius LLP

(57) ABSTRACT

The disclosure provides a delayed fluorescent compound of the Formula

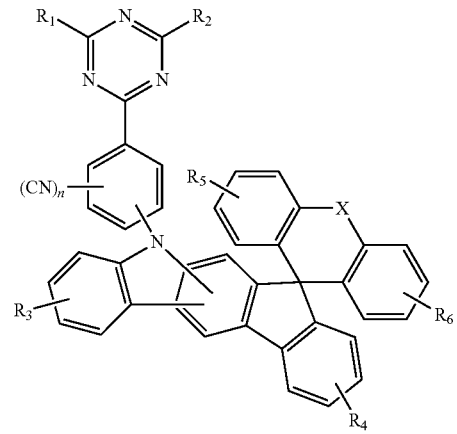

and an organic light emitting diode including a first electrode, a second electrode and an organic emitting layer between the first and second electrodes, where the delayed fluorescent compound is included in the organic emitting layer, and an organic light emitting display device including the organic emitting layer.

18 Claims, 3 Drawing Sheets

100

D

DELAYED FLUORESCENT COMPOUND, AND ORGANIC LIGHT EMITTING DIODE AND ORGANIC LIGHT EMITTING DISPLAY DEVICE INCLUDING THE SAME

CROSS-REFERENCE TO RELATED APPLICATIONS

This application claims the benefit under 35 U.S.C. § 119(a) of Korean Patent Application No. 10-2018-0170831 filed in Korea on Dec. 27, 2018, which is incorporated herein by reference in its entirety.

BACKGROUND

Technical Field

The present disclosure relates to a delayed fluorescent compound, and more particularly, to a delayed fluorescent compound having high emitting efficiency and an organic light emitting diode and an organic light emitting display device including the same.

Description of the Related Art

Requirements for flat panel display devices having small occupied areas have recently increased. Among flat panel display devices, the technology associated with an organic light emitting display device including an organic light emitting diode (OLED) has rapidly developed.

The OLED emits light by injecting electrons from a cathode acting as an electron injection electrode and holes from an anode acting as a hole injection electrode into an emitting layer, combining the electrons with the holes, generating excitons, and transforming the excitons from an excited state to a ground state. A flexible transparent substrate, for example, a plastic substrate, can be used as a base substrate where elements are formed. In addition, the emitting diode can be operated at a voltage (e.g., 10V or below) lower than the voltage required to operate other display devices and has low power consumption. Moreover, the light from the emitting diode has excellent color purity.

The hole from the anode and the electron from the cathode are combined in an emitting material layer (EML) to generate an exciton, and the exciton is transformed from an excited state to a ground state such that the light is emitted from the organic emitting layer.

A fluorescent material (compound) is widely used as an emitting material of the EML. However, since only a singlet exciton is involved in light emission, the fluorescent material provides only low emitting efficiency (quantum efficiency).

SUMMARY

The present disclosure is directed to a delayed fluorescent compound and an OLED and an organic light emitting display device including the same that substantially obviate one or more of the problems associated with the limitations and disadvantages of the related conventional art.

Additional features and advantages of the present disclosure are set forth in the description which follows, and will be apparent from the description, or evident by practice of the present disclosure. The objectives and other advantages of the present disclosure are realized and attained by the features described herein as well as in the appended drawings.

To achieve these and other advantages in accordance with the purpose of the embodiments of the present disclosure, as described herein, a delayed fluorescent compound of Formula:

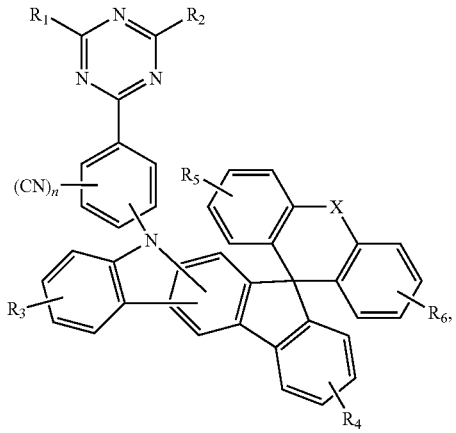

wherein X is oxygen (O) or sulfur (S), and each of $R_1$ to $R_6$ is independently selected from the group consisting of hydrogen, a C1 to C20 alkyl group, a C1 to C20 alkoxy group, a C6 to C30 aryl group, a C5 to C30 heteroaryl group and a C1 to C20 amine group, and wherein n is an integer of 1 to 4.

Another aspect of the present disclosure is an organic light emitting diode comprising: a first electrode; a second electrode facing the first electrode; and a first emitting material layer positioned between the first and second electrodes and including a delayed fluorescent compound, wherein the delayed fluorescent compound is represented by Formula:

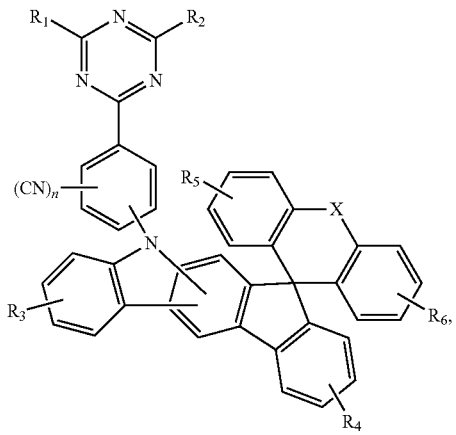

wherein X is oxygen (O) or sulfur (S), and each of $R_1$ to $R_6$ is independently selected from the group consisting of hydrogen, a C1 to C20 alkyl group, a C1 to C20 alkoxy group, a C6 to C30 aryl group, a C5 to C30 heteroaryl group and a C1 to C20 amine group, and wherein n is an integer of 1 to 4.

Another aspect of the present disclosure is an organic light emitting display device comprising: a substrate; and an organic light emitting diode on the substrate, the organic light emitting diode including: a first electrode; a second electrode facing the first electrode; and a first emitting material layer positioned between the first and second electrodes and including a delayed fluorescent compound, wherein the delayed fluorescent compound is represented by Formula:

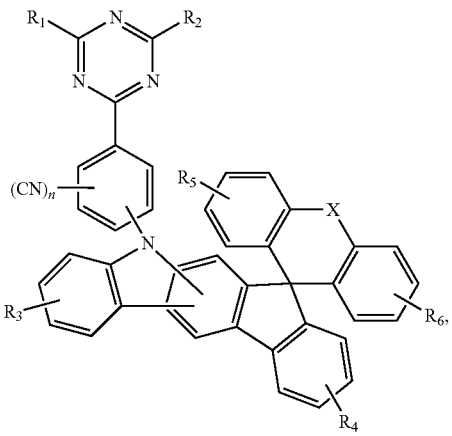

wherein X is oxygen (O) or sulfur (S), and each of $R_1$ to $R_6$ is independently selected from the group consisting of hydrogen, a C1 to C20 alkyl group, a C1 to C20 alkoxy group, a C6 to C30 aryl group, a C5 to C30 heteroaryl group and a C1 to C20 amine group, and wherein n is an integer of 1 to 4.

It is to be understood that both the foregoing general description and the following detailed description are exemplary and explanatory and are intended to further explain the present disclosure as claimed.

BRIEF DESCRIPTION OF THE DRAWINGS

The accompanying drawings, which are included to provide a further understanding of the present disclosure and are incorporated in and constitute a part of this specification, illustrate embodiments of the present disclosure and together with the description serve to explain the principles of the present disclosure.

DETAILED DESCRIPTION

Reference will now be made in detail to some of the examples and preferred embodiments, which are illustrated in the accompanying drawings.

Figure 1:
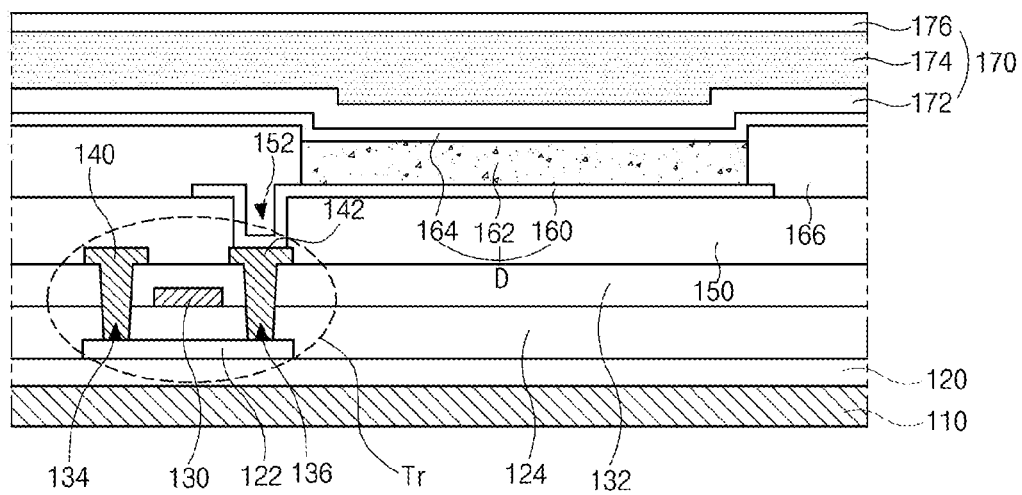
FIG. 1 is a schematic cross-sectional view of an organic light emitting display device of the present disclosure.

FIG. 1 is a schematic cross-sectional view of an organic light emitting display device of the present disclosure.

As shown in FIG. 1, the organic light emitting display device 100 includes a substrate 110, a TFT Tr and an OLED D connected to the TFT Tr.

The substrate 110 may be a glass substrate or a plastic substrate. For example, the substrate 110 may be a polyimide substrate.

A buffer layer 120 is formed on the substrate, and the TFT Tr is formed on the buffer layer 120. The buffer layer 120 may be omitted.

A semiconductor layer 122 is formed on the buffer layer 120. The semiconductor layer 122 may include an oxide semiconductor material or polycrystalline silicon.

When the semiconductor layer 122 includes an oxide semiconductor material, a light-shielding pattern (not shown) may be formed under the semiconductor layer 122. The light to the semiconductor layer 122 is shielded or blocked by the light-shielding pattern such that thermal degradation of the semiconductor layer 122 can be prevented. On the other hand, when the semiconductor layer 122 includes polycrystalline silicon, impurities may be doped into both sides of the semiconductor layer 122.

A gate insulating layer 124 is formed on the semiconductor layer 122. The gate insulating layer 124 may be formed of an inorganic insulating material such as silicon oxide or silicon nitride.

A gate electrode 130, which is formed of a conductive material (e.g., a metal), is formed on the gate insulating layer 124 to correspond to the center of the semiconductor layer 122.

In FIG. 1, the gate insulating layer 124 is formed on an entire surface of the substrate 110. Alternatively, the gate insulating layer 124 may be patterned to have the same shape as the gate electrode 130.

An interlayer insulating layer 132, which is formed of an insulating material, is formed on the gate electrode 130. The interlayer insulating layer 132 may be formed of an inorganic insulating material (e.g., silicon oxide or silicon nitride), or an organic insulating material (e.g., benzocyclobutene or photo-acryl).

The interlayer insulating layer 132 includes first and second contact holes 134 and 136 exposing both sides of the semiconductor layer 122. The first and second contact holes 134 and 136 are positioned at both sides of the gate electrode 130 to be spaced apart from the gate electrode 130.

The first and second contact holes 134 and 136 are formed through the gate insulating layer 124. Alternatively, when the gate insulating layer 124 is patterned to have the same shape as the gate electrode 130, the first and second contact holes 134 and 136 are formed only through the interlayer insulating layer 132.

A source electrode 140 and a drain electrode 142, which are formed of a conductive material (e.g., a metal), are formed on the interlayer insulating layer 132.

The source electrode 140 and the drain electrode 142 are spaced apart from each other with respect to the gate electrode 130 and respectively contact both sides of the semiconductor layer 122 through the first and second contact holes 134 and 136.

The semiconductor layer 122, the gate electrode 130, the source electrode 140 and the drain electrode 142 constitute the TFT Tr. The TFT Tr serves as a driving element.

In the TFT Tr, the gate electrode 130, the source electrode 140, and the drain electrode 142 are positioned over the semiconductor layer 122. In this embodiment, the TFT Tr has a coplanar structure.

Alternatively, in the TFT Tr, the gate electrode may be positioned under the semiconductor layer, and the source and drain electrodes may be positioned over the semiconductor layer such that the TFT Tr may have an inverted staggered structure. In this instance, the semiconductor layer may include amorphous silicon.

Although not shown, the gate line and the data line cross each other to define the pixel region, and the switching TFT is formed to be connected to the gate and data lines. The switching TFT is connected to the TFT Tr as the driving element.

In addition, the power line, which may be formed to be parallel to and spaced apart from one of the gate and data lines, and the storage capacitor for maintaining the voltage of the gate electrode of the TFT Tr in one frame may be further formed.

A passivation layer 150, which includes a drain contact hole 152 exposing the drain electrode 142 of the TFT Tr, is formed to cover the TFT Tr.

A first electrode 160, which is connected to the drain electrode 142 of the TFT Tr through the drain contact hole 152, is separately formed in each pixel region. The first electrode 160 may be an anode and may be formed of a conductive material having a relatively high work function. For example, the first electrode 160 may be formed of a transparent conductive material such as indium-tin-oxide (ITO) or indium-zinc-oxide (IZO).

When the OLED device 100 is operated in a top-emission type, a reflection electrode or a reflection layer may be formed under the first electrode 160. For example, the reflection electrode or the reflection layer may be formed of an aluminum-palladium-copper (APC) alloy.

A bank layer 166 is formed on the passivation layer 150 to cover an edge of the first electrode 160. Namely, the bank layer 166 is positioned at a boundary of the pixel region and exposes a center of the first electrode 160 in the pixel region.

An organic emitting layer 162 is formed on the first electrode 160. The organic emitting layer 162 includes a delayed fluorescent compound of the present disclosure. As described below, the delayed fluorescent compound of the present disclosure includes a triazine moiety and a spiroindeno(thio)xanthen moiety such that high emitting efficiency is provided.

When the organic light emitting display device 100 includes a red pixel region, a green pixel region and a blue pixel region, the organic emitting layer 162 may include a red emitting pattern, a green emitting pattern and a blue emitting pattern. The delayed fluorescent compound of the present disclosure is included in the organic emitting layer 162 in the green pixel region, i.e., the green emitting pattern.

The organic emitting layer 162 may have a single-layered structure of an emitting material layer including the organic emitting compound. To increase the emitting efficiency of the OLED device, the organic emitting layer 162 may have a multi-layered structure. For example, the organic emitting layer 162 may include a hole injection layer (HIL), a hole transporting layer (HTL), the EML, an electron transporting layer (ETL) and an electron injection layer (EIL) sequentially stacked on the first electrode (160). In addition, the organic emitting layer 162 may further include an electron blocking layer (EBL) between the HTL and the EML, and a hole blocking layer (HBL) between the EML and the ETL.

A second electrode 164 is formed over the substrate 110 where the organic emitting layer 162 is formed. The second electrode 164 covers an entire surface of the display area and may be formed of a conductive material having a relatively low work function to serve as a cathode. For example, the second electrode 164 may be formed of aluminum (Al), magnesium (Mg) or an Al—Mg alloy.

The first electrode 160, the organic emitting layer 162 and the second electrode 164 constitute the OLED D.

An encapsulation film 170 is formed on the second electrode 164 to prevent penetration of moisture into the OLED D. The encapsulation film 170 includes a first inorganic insulating layer 172, an organic insulating layer 174 and a second inorganic insulating layer 176 sequentially stacked, but it is not limited thereto. The encapsulation film 170 may also be omitted.

A polarization plate (not shown) for reducing an ambient light reflection may be disposed over the top-emission type OLED D. For example, the polarization plate may be a circular polarization plate.

In addition, a cover window (not shown) may be attached to the encapsulation film 170 or the polarization plate. In this instance, the substrate 110 and the cover window have a flexible property such that a flexible display device may be provided.

Figure 2:
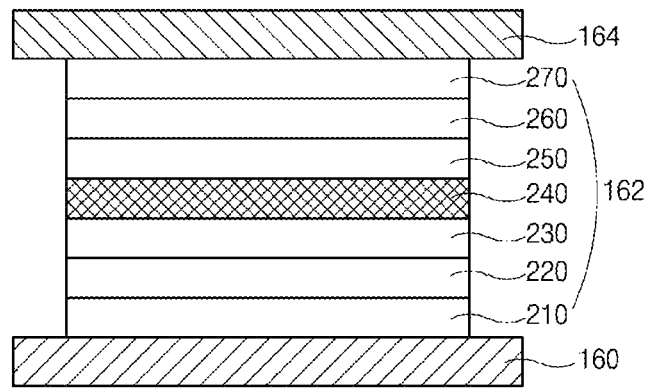
FIG. 2 is a schematic-cross sectional view of an OLED according to a first embodiment of the present disclosure.

FIG. 2 is a schematic-cross sectional view of an OLED according to a first embodiment of the present disclosure.

As shown in FIG. 2, the OLED D includes the first and second electrodes 160 and 164, which face each other, and the organic emitting layer 162 therebetween. The organic emitting layer 162 includes an emitting material layer (EML) 240 between the first and second electrodes 160 and 164, a hole transporting layer (HTL) 220 between the first electrode 160 and the EML 240 and an electron transporting layer (ETL) 260 between the second electrode 164 and the EML 240.

In addition, the organic emitting layer 162 may further include a hole injection layer (HIL) 210 between the first electrode 160 and the HTL 220, and an electron injection layer (EIL) 270 between the second electrode 164 and the ETL 260.

Moreover, the organic emitting layer 162 may further include an electron blocking layer (EBL) 230 between the HTL 220 and the EML 240, and a hole blocking layer (HBL) 250 between the EML 240 and the ETL 260.

The organic emitting layer 162, preferably the EML 240 includes the delayed fluorescent compound of the present disclosure. The delayed fluorescent compound may also be used as a dopant.

The delayed fluorescent compound of the present disclosure includes a triazine moiety and a spiroindeno(thio)xanthen moiety. The delayed fluorescent compound may be represented by Formula 1.

[Formula 1]

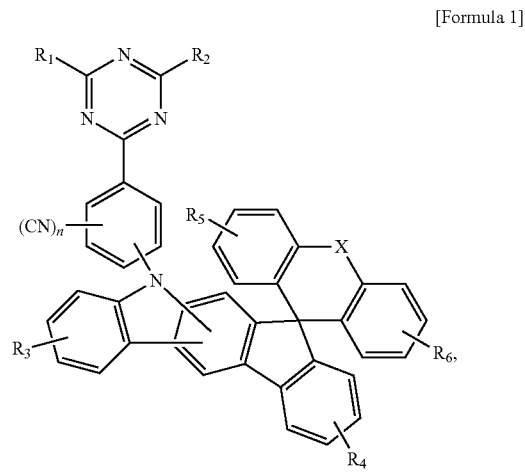

In Formula 1, X is oxygen (O) or sulfur (S). Each of $R_1$ to $R_6$ is independently selected from the group consisting of hydrogen, a C1 to C20 alkyl group, a C1 to C20 alkoxy group, a C6 to C30 aryl group, a C5 to C30 heteroaryl group and a C1 to C20 amine group, and "n" is an integer of 1 to 4. In an embodiment, the C1 to C20 amine group may be substituted by a C6 to C30 aryl group or by a C5 to C30 heteroaryl group.

In an exemplary embodiment, each of $R_1$ and $R_2$ is independently selected from a C6 to C30 aryl group, each of $R_3$ to $R_6$ is hydrogen, and "n" is 1 or 2.

In the delayed fluorescent compound, the electron donor moiety and the electron acceptor moiety are bonded (combined or linked) in the molecule such that an overlap between the highest occupied molecular orbital (HOMO) and the lowest unoccupied molecular orbital (LUMO) is reduced. As a result, a charge transfer complex is generated, and the emitting efficiency of the delayed fluorescent compound is improved. Namely, in the delayed fluorescent compound, the triplet exciton is used for emission such that the emitting efficiency is improved.

In other words, since the delayed fluorescent compound of the present disclosure includes an electron acceptor moiety of a triazine and an electron donor moiety of a spiroindeno(thio)xanthen, the charge transfer is efficiently generated and the emission efficiency is improved.

In addition, in the delayed fluorescent compound of the present disclosure, since the electron acceptor moiety of a triazine and the electron donor moiety of a spiroindeno(thio) xanthen are bonded to a phenylene linker at a para-position and at least one cyano (CN) group is bonded to the phenylene linker, the delayed fluorescent compound provides green light with high efficiency.

Figure 3:
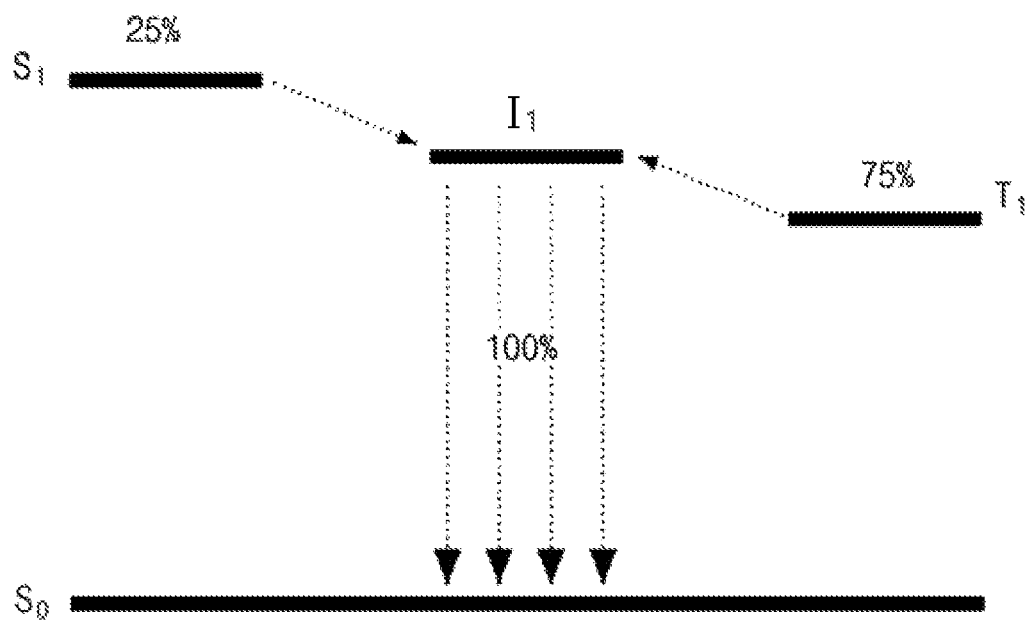
FIG. 3 is a view illustrating an emission mechanism of a delayed fluorescent compound according to the present disclosure.

Referring to FIG. 3, which is a view illustrating an emission mechanism of a delayed fluorescent compound according to the present disclosure, the triplet excitons as well as the singlet excitons are engaged in the emission such that the emitting efficiency is improved.

Namely, the triplet exciton is activated by a field or heat, and the triplet exciton and the singlet exciton are transferred into an intermediated state "$I_1$" and transited into a ground state "So" to emit the light. In other words, the singlet state "$S_1$" and the triplet state "$T_1$" are transited into the intermediated state "$I_1$" ($S_1 \rightarrow I_1 \leftarrow T_1$), and the singlet exciton and the triplet exciton in the intermediated state "$I_1$" are involved in the light emission such that the emitting efficiency is improved.

In a related art fluorescence compound, since the HOMO and the LUMO are dispersed throughout an entirety of the molecule, the interconversion of the HOMO and the LUMO is impossible. (Selection Rule.)

However, in the delayed fluorescent compound of the present invention, since the overlap between the HOMO and the LUMO in the molecule is relatively small, the interaction between the HOMO and the LUMO is also small. Accordingly, changes of the spin state of one electron do not affect other electrons, and a new charge transfer band, which does not comply with the Selection Rule, is generated.

Moreover, since the electron donor moiety and the electron acceptor moiety are spaced apart from each other in the molecule, the dipole moment is generated in a polarized state. In the polarized state dipole moment, the interaction between the HOMO and the LUMO is further reduced such that the emission mechanism does not comply with the Selection Rule. Accordingly, in the delayed fluorescent compound, the transition from the triplet state "$T_1$" and the singlet state "$S_1$" into the intermediated state "$I_1$" can be generated such that the triplet exciton can be involved in the light emission.

When the OLED is driven, the intersystem transition (intersystem crossing) from 25% singlet state "$S_1$" excitons and 75% triplet state "$T_1$" excitons to the intermediated state "$I_1$" is generated, and the singlet and triplet excitons in the intermediated state "$I_1$" are transited into the ground state to emit the light. As a result, the delayed fluorescent compound has the theoretic quantum efficiency of 100%.

In an exemplary embodiment, the delayed fluorescent compound of Formula 1 may be selected from the compounds of Formula 2. [Formula 2]

[Formula 2]

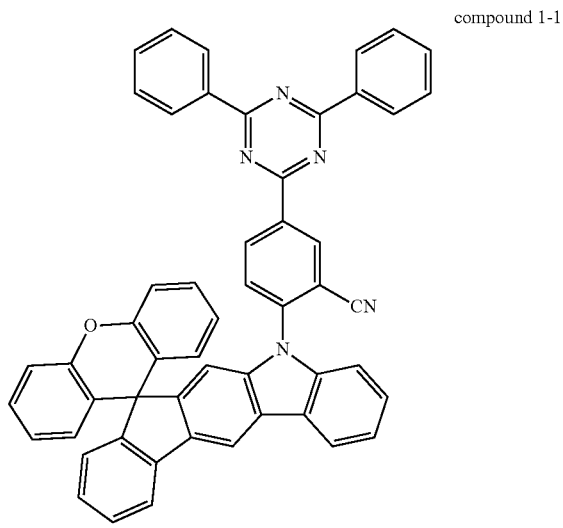 [SMILES: c1ccc(-c2nc(-c3ccccc3)nc(-c3ccc(-n4c5ccccc5c5cc6c(cc54)C4(c5ccccc5Oc5ccccc54)c4ccccc4-6)cc3)n2)cc1]

compound 1-1

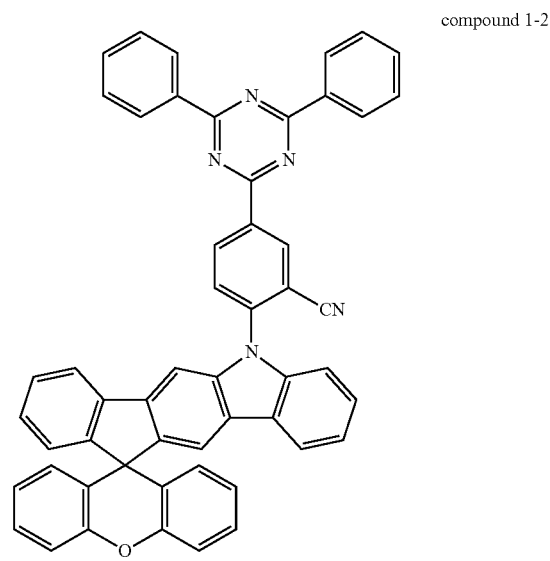

compound 1-2 compound 1-3
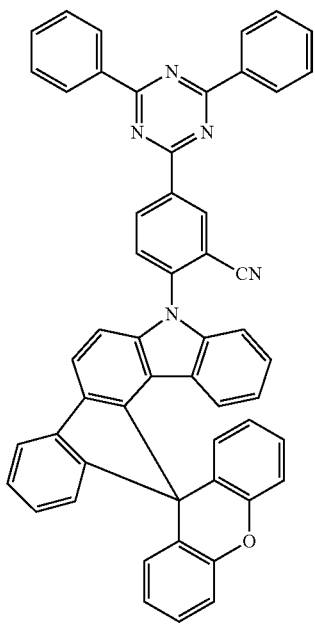
compound 1-4
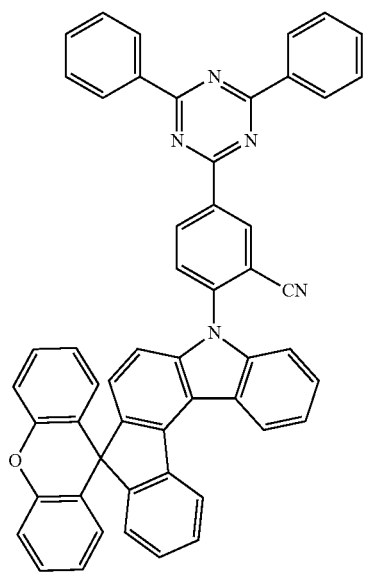
compound 1-5
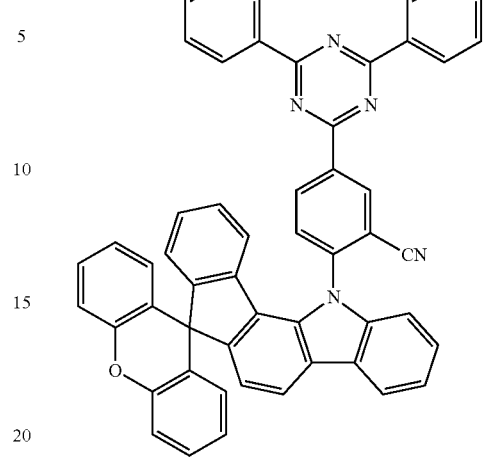
compound 1-6
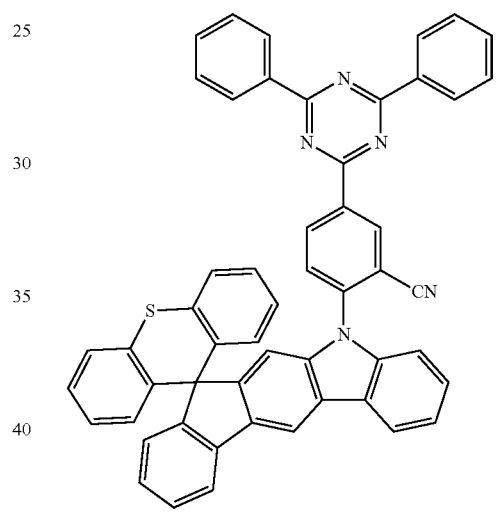
compound 1-7
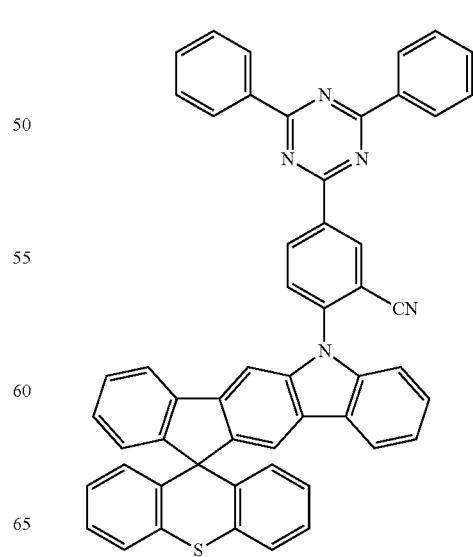

compound 1-8
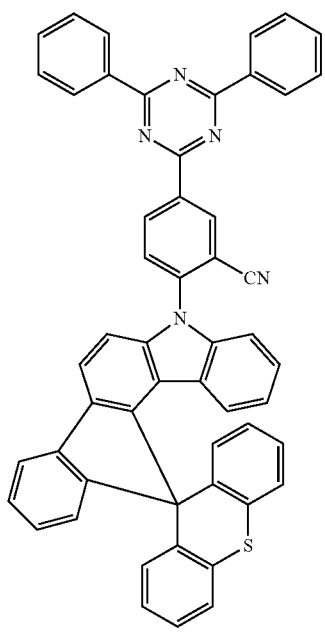
compound 1-10
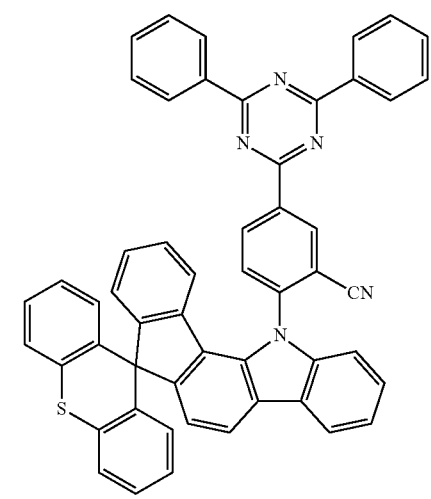
compound 2-1
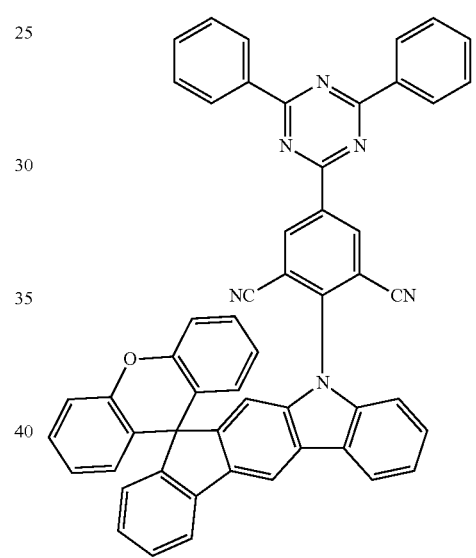
compound 1-9
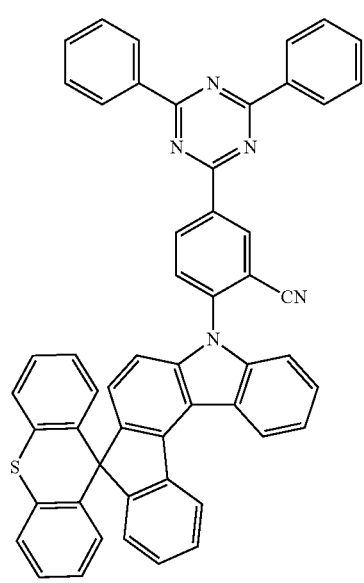
compound 2-2
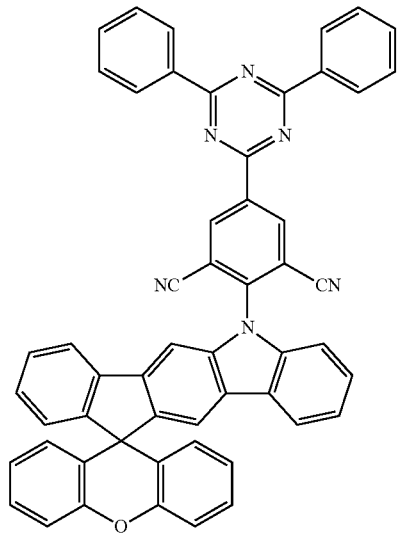

compound 2-3
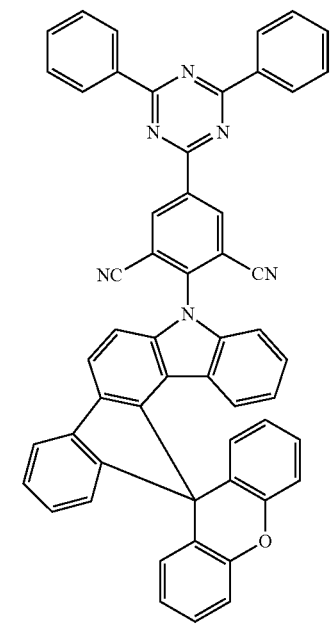
compound 2-4
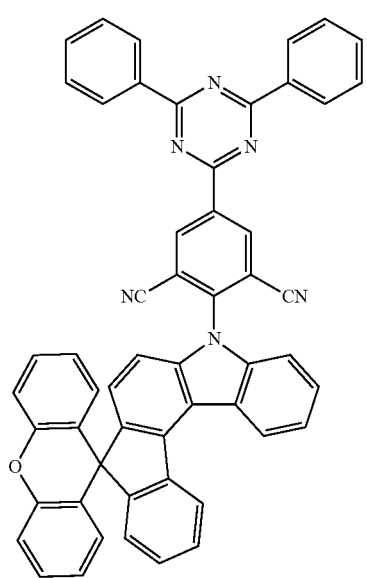
compound 2-5
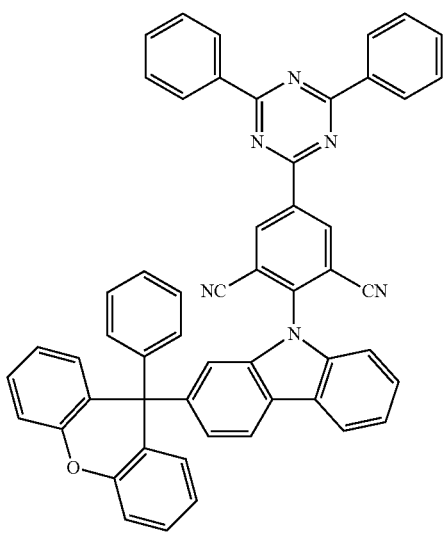
compound 2-6
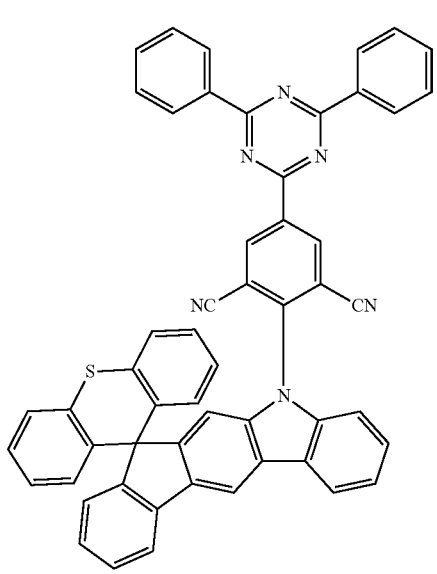
compound 2-7
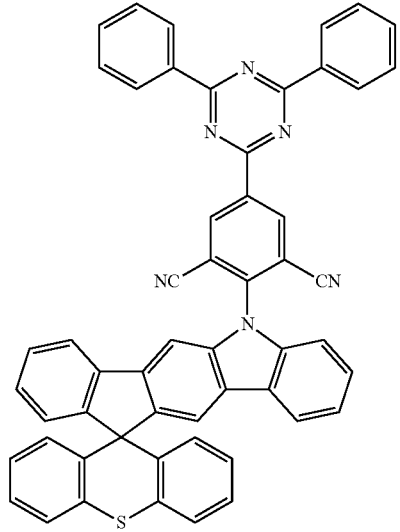

compound 2-8
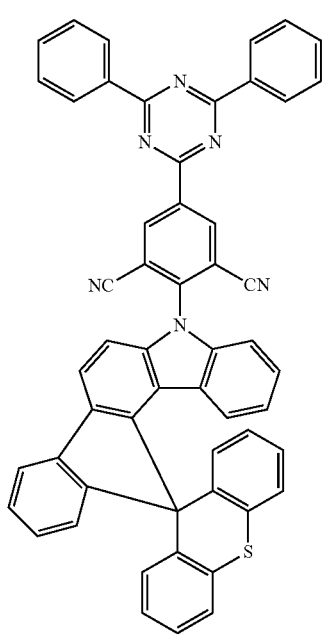
compound 2-9
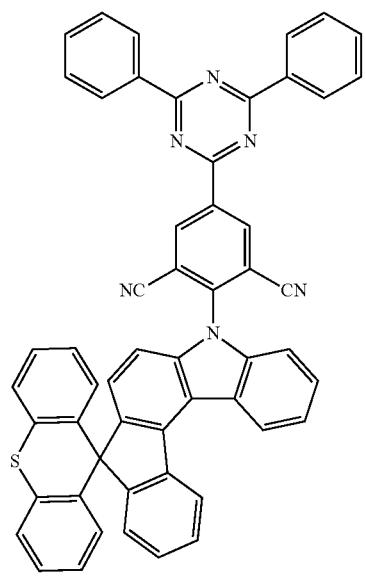
compound 2-10
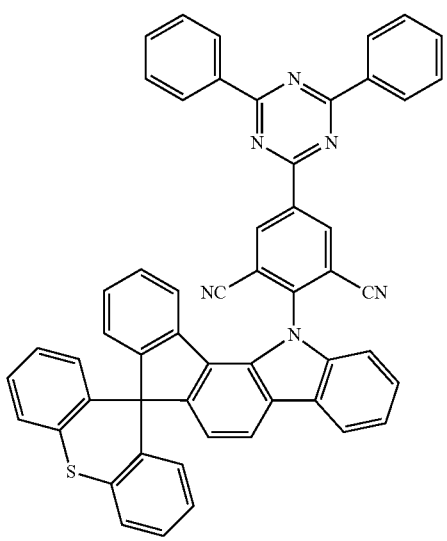
compound 3-1
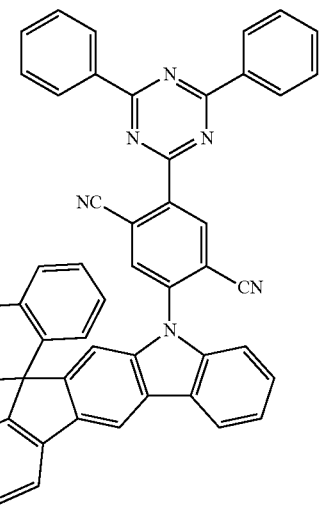
compound 3-2
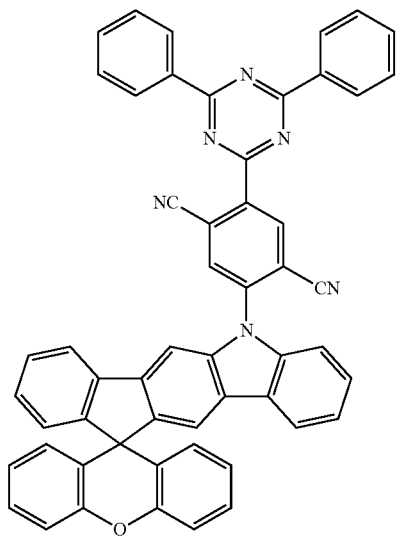

compound 3-3
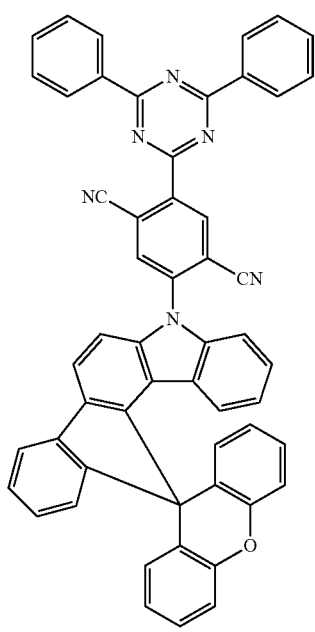
compound 3-5
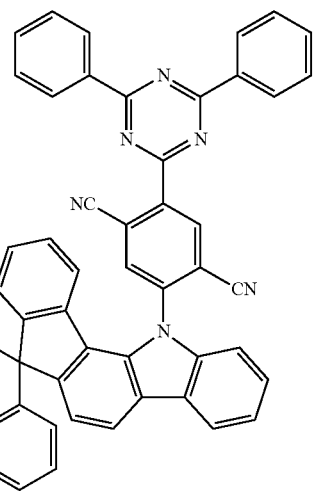
compound 3-6
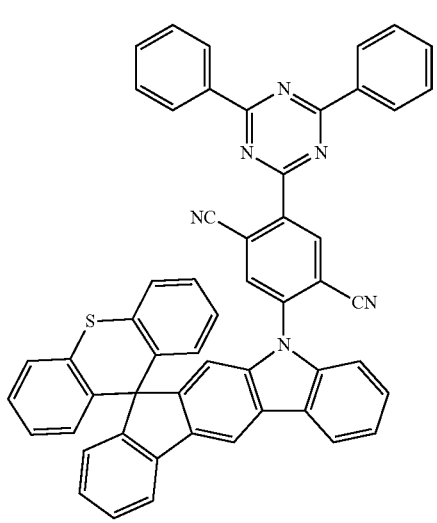
compound 3-4
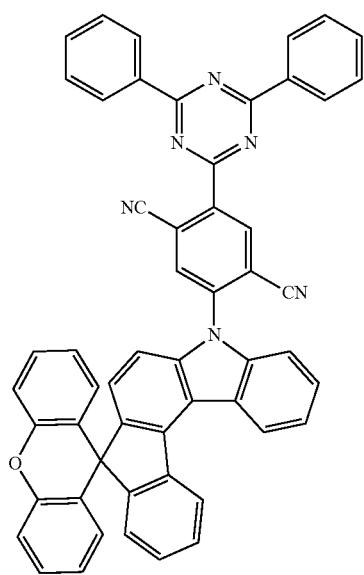
compound 3-7
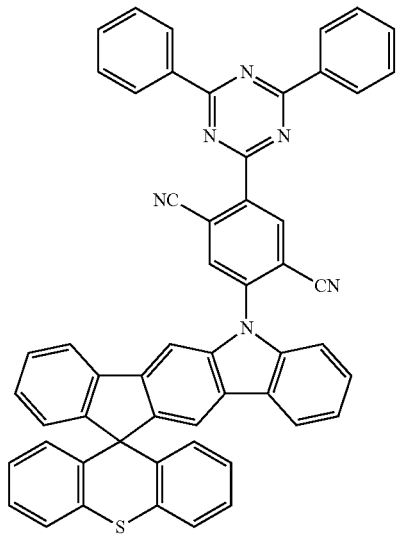

compound 3-8
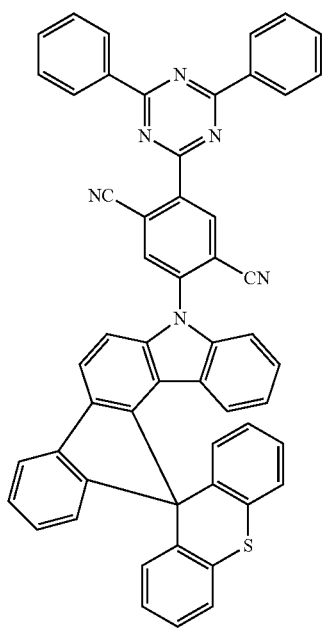
compound 3-9
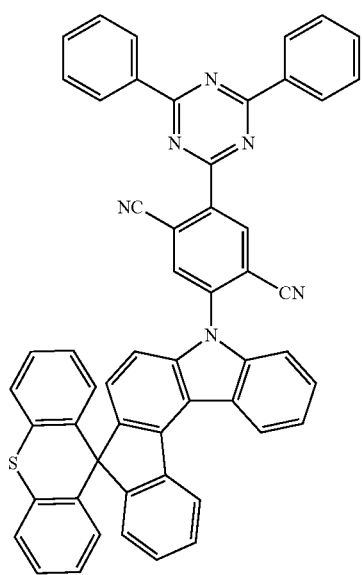
compound 3-10
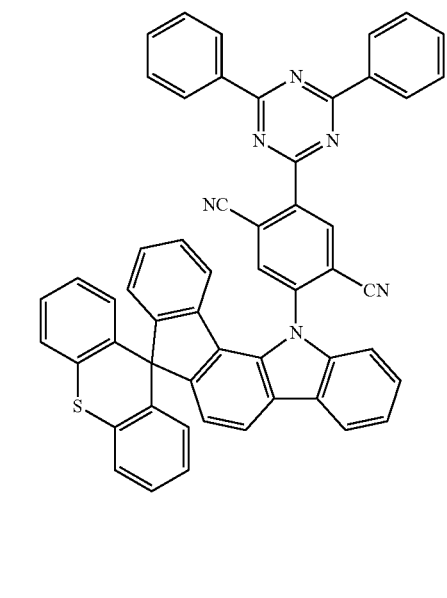
compound 4-1
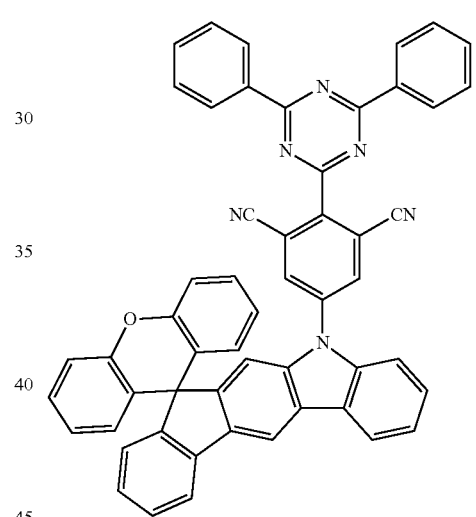
compound 4-2
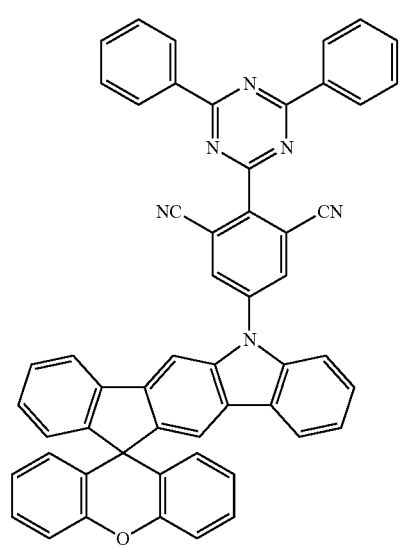

-continued
compound 4-3
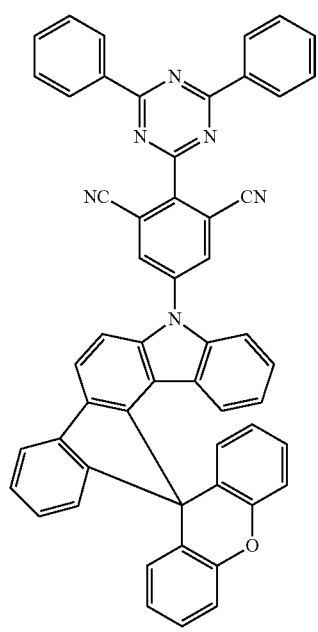
compound 4-4
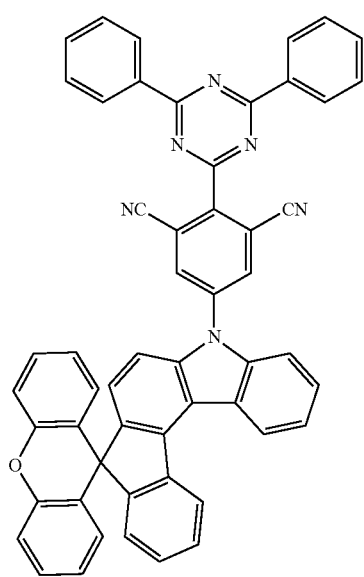
compound 4-5
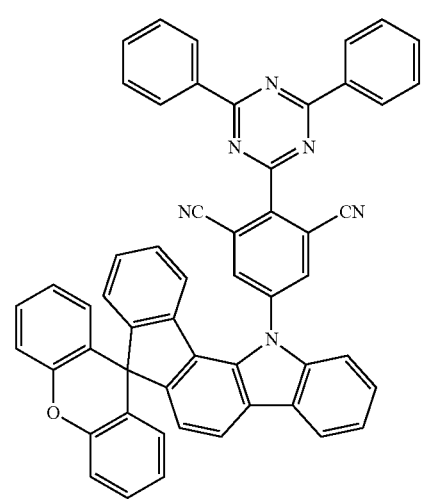
compound 4-6
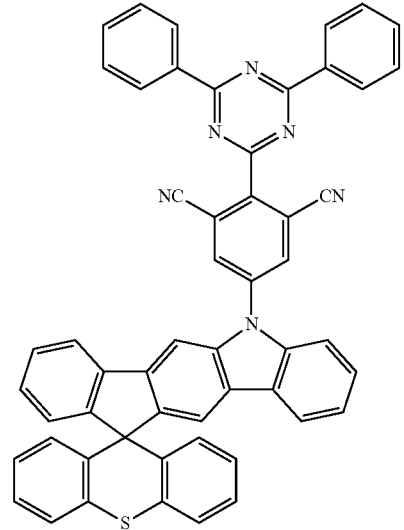
compound 4-7 compound 4-8

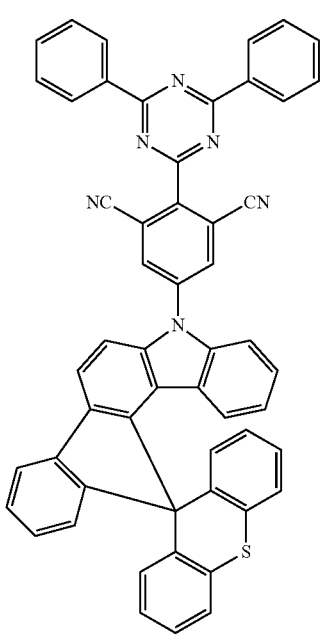

compound 4-10

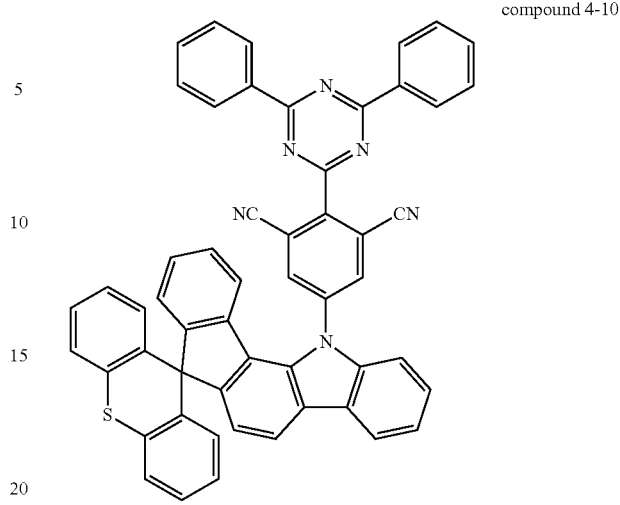

Synthesis of Delayed Fluorescent Compounds
1. Synthesis of Compound 1-1
(1) Compound A-1

[Reaction Formula 1-1]

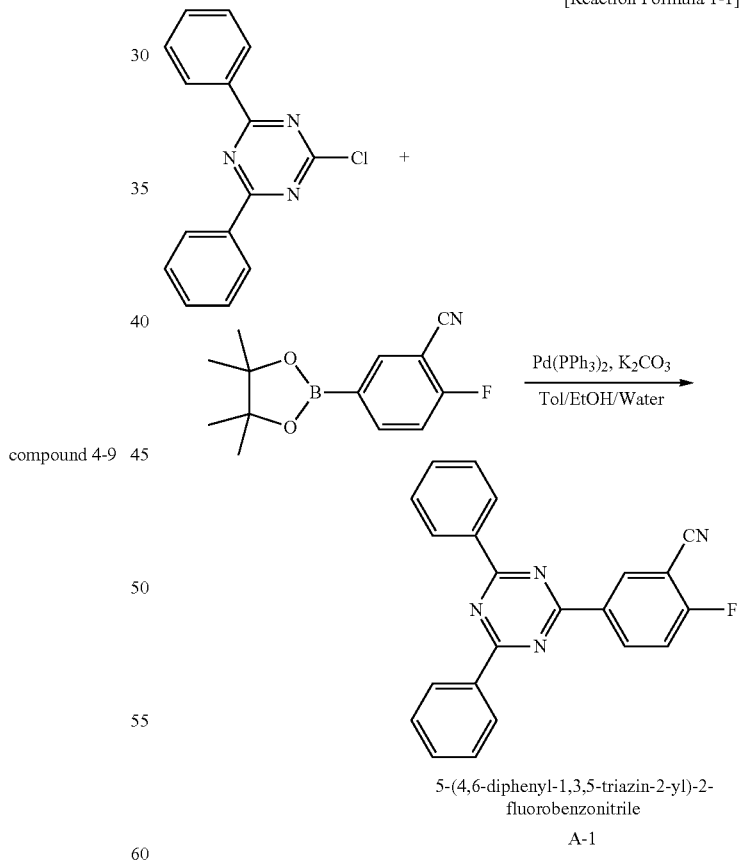

5-(4,6-diphenyl-1,3,5-triazin-2-yl)-2-fluorobenzonitrile
A-1 compound 4-9

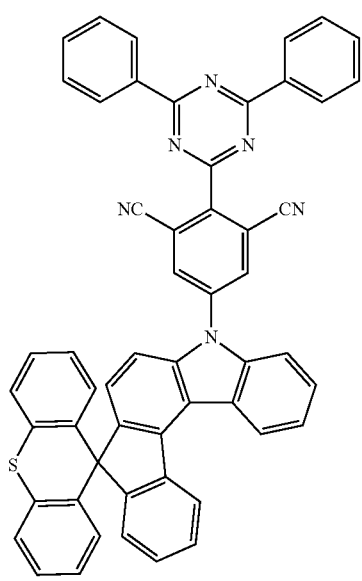

In a two-neck flask (500 ml), 2-chloro-4,6-diphenyl-1,3,5-triazine (2.00 g, 7.47 mmol), 2-fluoro-5-(4,4,5,5-tetramethyl-1,3,2-dioxaborolan-2-yl)benzonitrile (2.77 g, 11.21 mmol), $K_2CO_3$ (5.16 g, 37.35 mmol) and Pd(PPh$_3$)$_4$ (0.26 g, 0.22 mmol) were dissolved in a mixed solvent of toluene, ethanol (EtOH) and water (volume ratio=3:1:1, 250 ml). The mixture was refluxed and stirred for 12 hrs. After completion of the reaction, the mixture was chromatographed using methylene chloride (MC) and hexane (volume ratio=3:7) such that the compound A-1 was obtained. (2.10 g, yield: 79.78%)

(2) Compound B-1

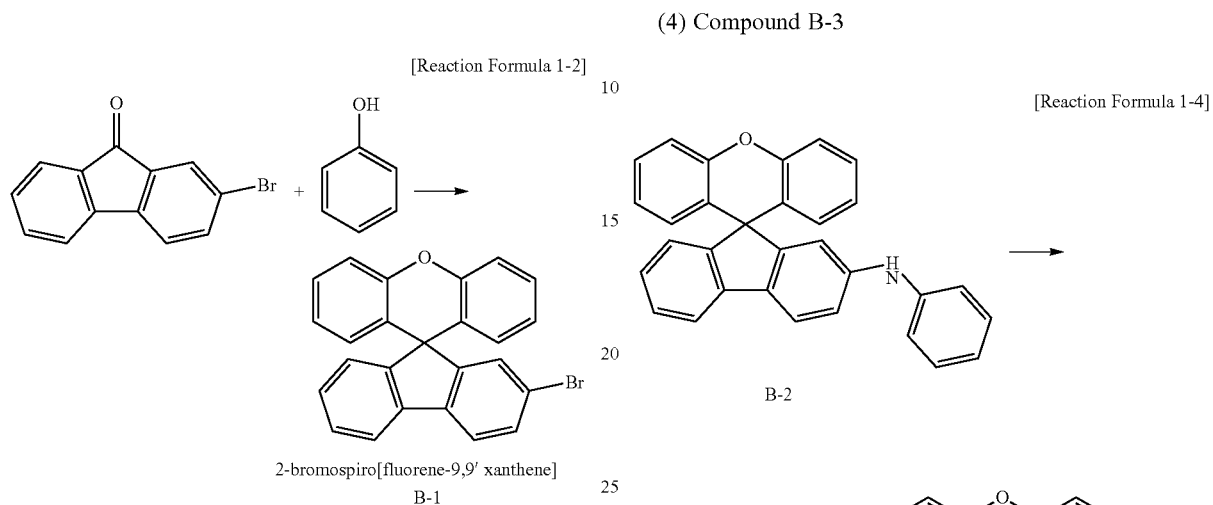

2-bromospiro[fluorene-9,9′ xanthene]
B-1

In a two-neck flask (1000 ml), 2-bromo-9H-fluoren-9-one (50 g, 193 mmol), phenol (170 ml, 1930 mmol) and methane sulfonic acid (50.1 ml, 771.9 mmol) were stirred under a temperature of 160° C. for 12 hrs. After completion of the reaction, the mixture was distilled under reduced-pressure. The resultant was chromatographed using silica-gel such that the compound B-1 was obtained. (43.6 g, yield: 55%)

(3) Compound B-2

[Reaction Formula 1-3]

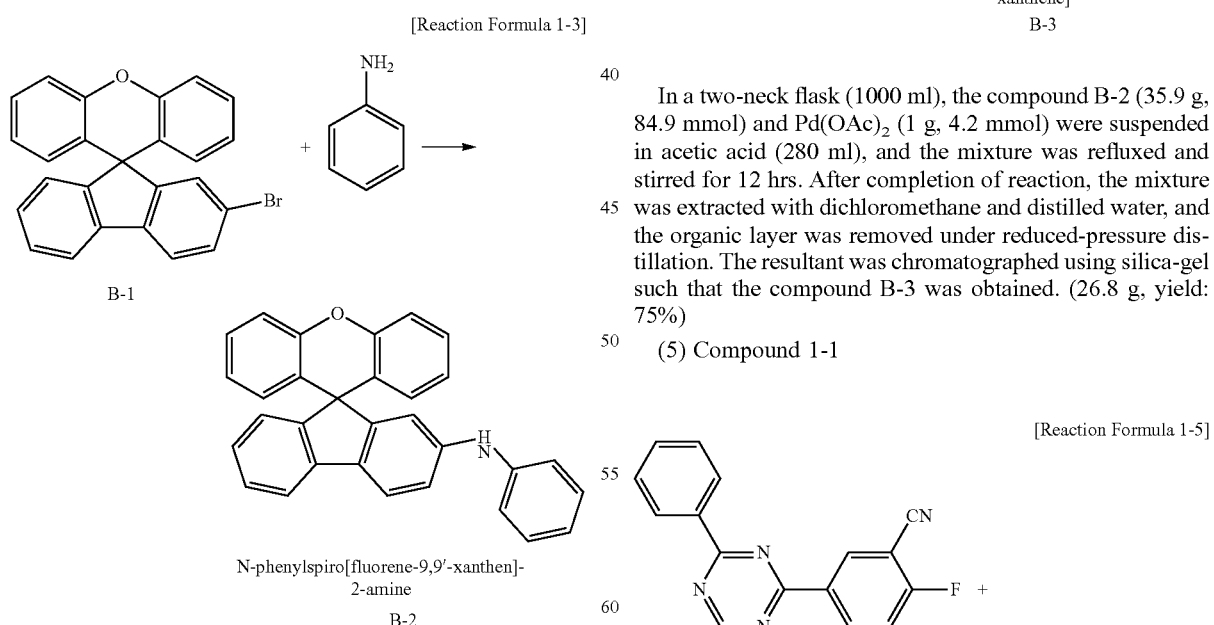

N-phenylspiro[fluorene-9,9′-xanthen]-2-amine
B-2

In a two-neck flask (1000 ml), the compound B-1 (43.6 g, 106.1 mmol), aniline (10.6 ml, 116.6 mmol), Pd₂(dba)₃ (1 g, 1.1 mmol), tri-tert-butylphosphine (50% in toluene) (0.51 ml, 1.1 mmol) and sodium-tert-butoxide (15.3 g, 159 mmol) were suspended in toluene (530 ml), and the mixture was refluxed and stirred for 12 hrs. After completion of the reaction, the mixture was extracted with dichloromethane and distilled water, and the organic layer was removed under reduced-pressure distillation. The resultant was silica-gel-columned such that the compound B-2 was obtained. (35.9 g, yield: 80%)

(4) Compound B-3

[Reaction Formula 1-4]

5H-spiro[indeno[2,1-b]carbazole-7,9′-xanthene]
B-3

In a two-neck flask (1000 ml), the compound B-2 (35.9 g, 84.9 mmol) and Pd(OAc)₂ (1 g, 4.2 mmol) were suspended in acetic acid (280 ml), and the mixture was refluxed and stirred for 12 hrs. After completion of reaction, the mixture was extracted with dichloromethane and distilled water, and the organic layer was removed under reduced-pressure distillation. The resultant was chromatographed using silica-gel such that the compound B-3 was obtained. (26.8 g, yield: 75%)

(5) Compound 1-1

[Reaction Formula 1-5]

A-1

-continued

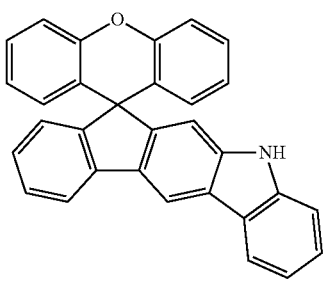

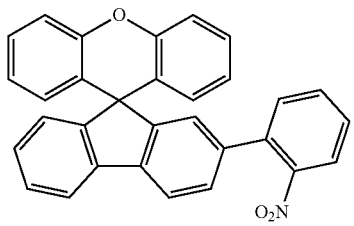

2-(2-nitrophenyl)spiro[fluorene 9-9′-xanthene]
C-1

In a two-neck flask (1000 ml), the compound B-1 (30 g, 72.9 mmol), 2-nitrophenyl boronic acid (13.4 g, 80.2 mmol), Pd(PPh$_3$)$_4$ (4.2 g, 3.6 mmol) and potassium carbonate (20.2 g, 145.9 mmol) were suspended in a mixed solvent of toluene (365 ml), ethyl alcohol (70 ml) and distilled water (70 ml), and the mixture was refluxed and stirred for 12 hrs. After completion of the reaction, the mixture was extracted with dichloromethane and distilled water, and the organic layer was removed under reduced-pressure distillation. The resultant was chromatographed using silica-gel such that the compound C-1 was obtained. (19.5 g, yield: 59%)

(2) Compound C-2

[Reaction Formula 2-2]

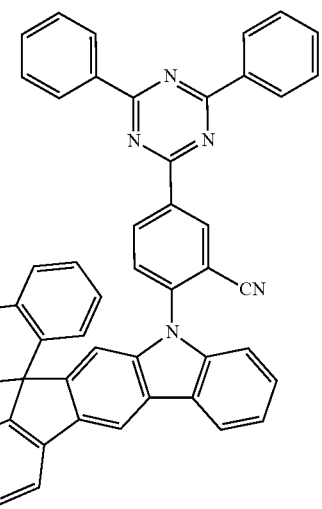

5-(4,6-diphenyl-1,3,5-triazin-2-yl)-2-(5H-spiro[ideno[2,1-b]carbazole-7,9′-xanthen]-5-yl]benzonitrile
B-3

In a two-neck flask (1000 ml), the compound A-1 (3.5 g, 9.9 mmol), the compound B-3 (4.2 g, 9.9 mmol) and cesium carbonate (6.5 g, 19.9 mmol) were suspended in dimethylformamide (DMF, 50 ml), and the mixture was stirred under a temperature of 190° C. for 16 hrs. After completion of the reaction, the mixture was extracted with dichloromethane and distilled water, and the organic layer was removed under reduced-pressure distillation. The resultant was silica-gel-columned such that the compound 1-A was obtained. (5.1 g, yield: 69%)

2. Synthesis of Compound 1-2

(1) Compound C-1

[Reaction Formula 2-1]

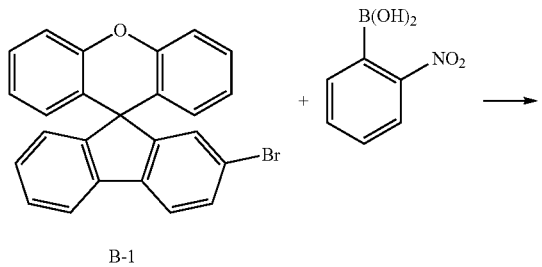

B-1

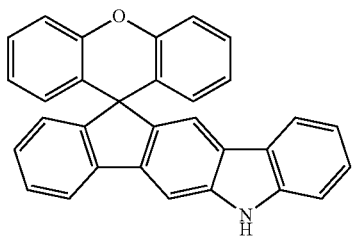

5H-spiro[indeno[1,2-b]carbazole-11,9′-xanthene]
C-2

In a two-neck flask (1000 ml), the compound C-1 (19.5 g, 43 mmol) and triphenylphosphine (33.8 g, 129 mmol) were suspended in 1,2-dichlorobenzene (220 ml), and the mixture was refluxed and stirred for 12 hrs. After completion of the reaction, the mixture was distilled under reduced-pressure distillation. The resultant was chromatographed using silica-gel such that the compound C-2 was obtained. (14.5 g, yield: 80%)

(3) Compound 1-2

3. Synthesis of Compound 1-3
(1) Compound D-1

[Reaction Formula 2-3]

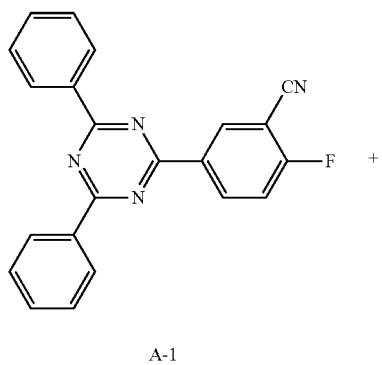

A-1

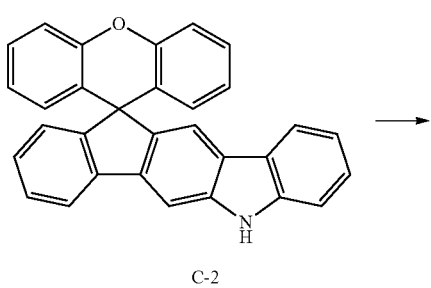

C-2

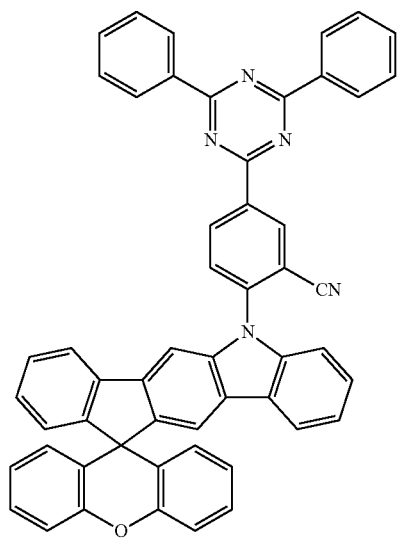

5-(4,6-diphenyl-1,3,5-triazin-2-yl)-2-(5H-spiro[indeno[1,2-b]carbazole-11,9'-xanthen]-5-yl)benzonitrile

[Reaction Formula 3-1]

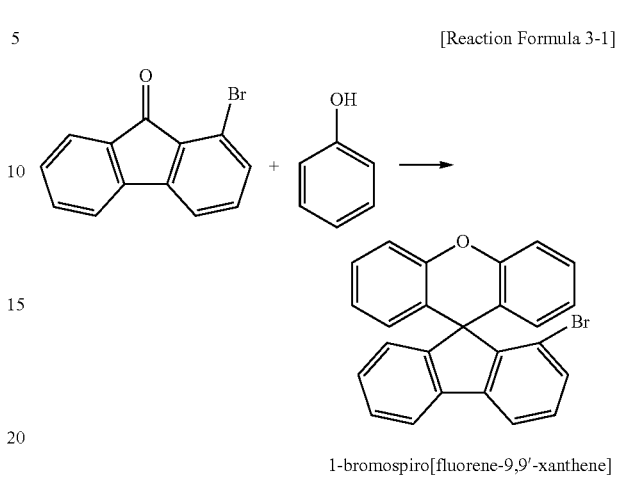

1-bromospiro[fluorene-9,9'-xanthene]
D-1

In a two-neck flask (1000 ml), 1-bromo-9H-fluoren-9-one (50 g, 193 mmol), phenol (169.7 ml, 1929.7 mmol) and methane sulfonic acid (50.1 ml, 74.2 mmol) were stirred under a temperature of 160° C. for 12 hrs. After completion of reaction, the mixture was distilled under reduced-pressure. The resultant was chromatographed using silica-gel such that the compound D-1 was obtained. (35.7 g, yield: 45%)

(2) Compound D-2

[Reaction Formula 3-2]

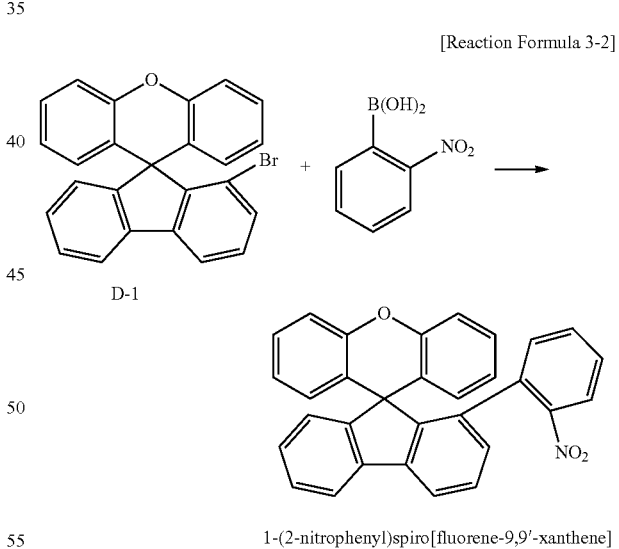

1-(2-nitrophenyl)spiro[fluorene-9,9'-xanthene]
D-2

In a two-neck flask (1000 ml), the compound A-1 (3.5 g, 9.9 mmol), the compound C-2 (4.2 g, 9.9 mmol) and cesium carbonate (6.5 g, 19.9 mmol) were suspended in DMF (50 ml), and the mixture was stirred under a temperature of 190° C. for 16 hrs. After completion of the reaction, the mixture was extracted with dichloromethane and distilled water, and the organic layer was removed under reduced-pressure distillation. The resultant was chromatographed using silica-gel such that the compound 1-2 was obtained. (4.5 g, yield: 60%)

In a two-neck flask (1000 ml) under nitrogen ($N_2$) conditions, the compound D-1 (35.7 g, 86.8 mmol), 2-nitrophenyl boronic acid (15.9 g, 95.5 mmol), Pd(PPh$_3$)$_4$ (5 g, 4.3 mmol) and potassium carbonate (24 g, 173.6 mmol) were suspended in a mixed solvent of toluene (430 ml), ethyl alcohol (85 ml) and distilled water (85 ml), and the mixture was refluxed and stirred for 12 hrs. After completion of the reaction, the mixture was extracted with dichloromethane and distilled water, and the organic layer was removed under reduced-pressure distillation. The resultant was chromatographed using silica-gel such that the compound D-2 was obtained. (13 g, yield: 33%)

(3) Compound D-3

[Reaction Formula 3-3]

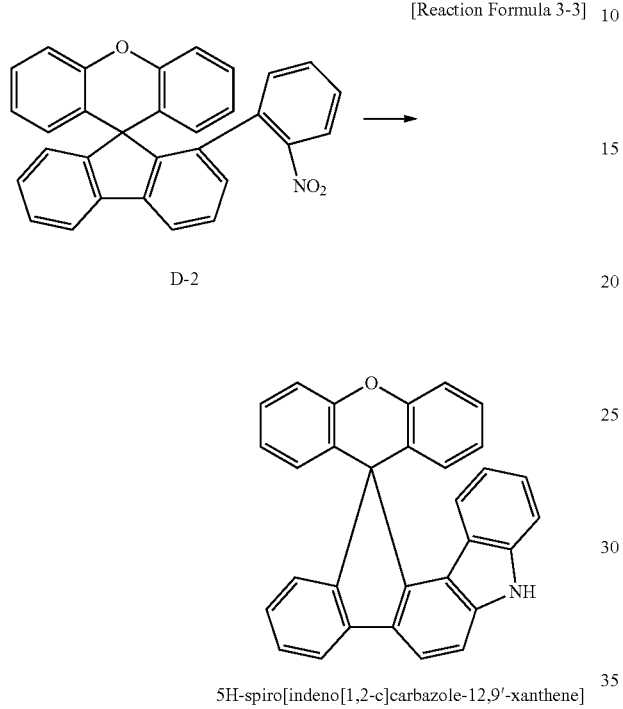

D-2

5H-spiro[indeno[1,2-c]carbazole-12,9'-xanthene]
D-3

In a two-neck flask (500 ml) under nitrogen (N$_2$) conditions, the compound D-2 (13 g, 28.6 mmol) and triphenylphosphine (22.5 g, 86 mmol) were suspended in 1,2-dichlorobenzene (145 ml), and the mixture was refluxed and stirred for 12 hrs. After completion of the reaction, the mixture was distilled under reduced-pressure. The resultant was chromatographed using silica-gel such that the compound D-3 was obtained. (7.23 g, yield: 60%)

(4) Compound 1-3

[Reaction Formula 3-4]

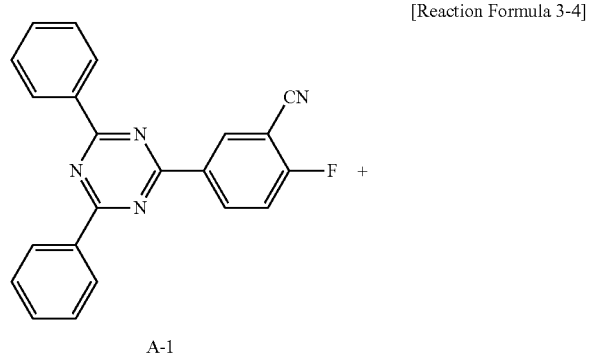

A-1

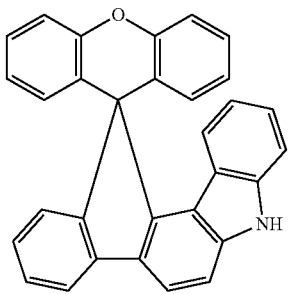

D-3

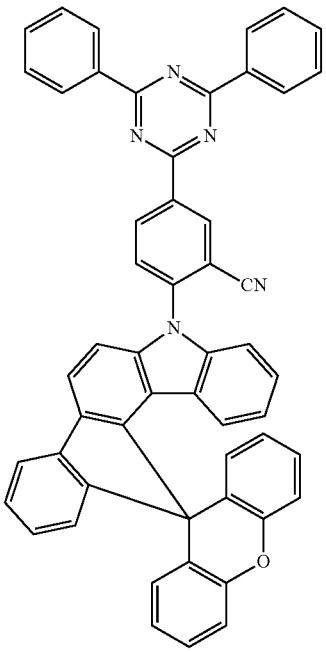

5-(4,6-diphenyl-1,3,5-triazin-2-yl)-2-
(5H-spiro[indeno[1,2-c]carbazole-
12,9'-xanthen]-5-yl)benzonitrile In a two-neck flask (1000 ml), the compound A-1 (3.5 g, 9.9 mmol), the compound D-3 (4.2 g, 9.9 mmol) and cesium carbonate (6.5 g, 19.9 mmol) were suspended in DMF (50 ml), and the mixture was stirred under a temperature of 190° C. for 16 hrs. After completion of the reaction, the mixture was extracted with dichloromethane and distilled water, and the organic layer was removed under reduced-pressure distillation. The resultant was chromatographed using silica-gel such that the compound 1-3 was obtained. (4.8 g, yield: 65%)

4. Synthesis of Compound 1-6

(1) Compound E-1

[Reaction Formula 4-1]

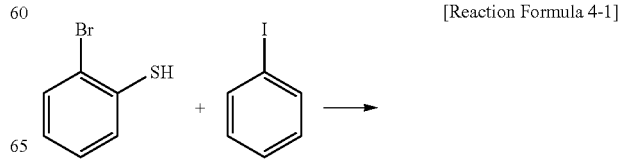

-continued

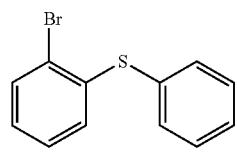

(2-bromophenyl)(phenyl)sulfane
E-1

In a two-neck flask (1000 ml), 2-bromo-benzenethiol (50 g, 264.4 mmol), iodobenzene (23.5 ml, 290.9 mmol), Pd(dba)$_2$ (7.6 g, 13.2 mmol), bis(diphenylphosphino)ferocene (7.3 g, 13.2 mmol) and sodium-tert-butoxide (38.1 g, 396.7 mmol) were suspended in toluene (1300 ml), and the mixture was refluxed and stirred for 12 hrs. After completion of the reaction, the mixture was filtered using celite. The resultant was distilled under reduced-pressure and chromatographed using silica-gel such that the compound E-1 was obtained. (35.1 g, yield: 70%)

(2) Compound E-2

[Reaction Formula 4-2]

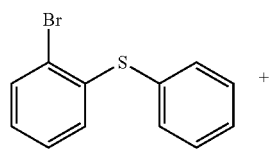

E-1

+

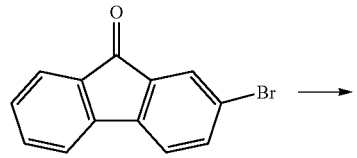

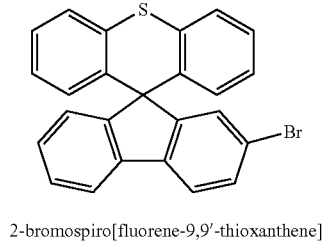

2-bromospiro[fluorene-9,9′-thioxanthene]

E-2

In a two-neck flask (1000 ml) under nitrogen (N$_2$) conditions, the compound E-1 (35.1 g, 132.3 mmol) was added to tetrahydrofuran (440 ml), and the mixture was cooled to a temperature of −78° C. using dry-ice. 2.5M n-butyllithium (58.2 ml, 145.53 mmol) was slowly added and the mixture was stirred for 1 hr. The solution, where 2-bromo-9H-fluorene-9-one (35.1 g, 132.3 mmol) was dissolved in tetrahydrofuran (330 ml), was slowly added to the mixture. Afterwards, the solvent was removed and the mixture was sufficiently dried. By adding a mixture of acetic acid and chloric acid (volume ratio=1:10, 400 ml) into the mixture, the compound E-2 was obtained. (40.5 g, yield=70%)

(3) Compound E-3

[Reaction Formula 4-3]

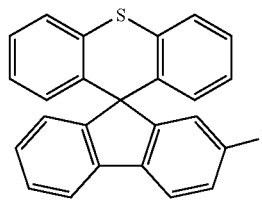

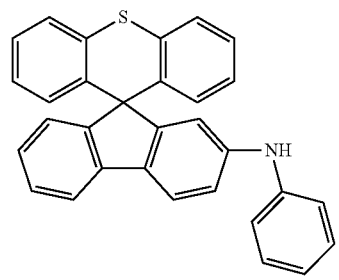

N-phenylspiro[fluorene-9-9′-thioxanthen]-2-amine

E-3

In a two-neck flask (500 ml), the compound E-2 (40.5 g, 94.8 mmol), aniline (9.5 ml, 104.2 mmol), Pd$_2$(dba)$_3$ (0.9 g, 0.9 mmol), tri-tert-butylphosphine (50% in toluene) (0.5 ml, 0.9 mmol) and sodium-tert-butoxide (13.6 g, 142.1 mmol) were suspended in toluene (470 ml), and the mixture was refluxed and stirred for 12 hrs. After completion of the reaction, the mixture was extracted with dichloromethane and distilled water, and the organic layer was removed under reduced-pressure distillation. The resultant was chromatographed using silica-gel such that the compound E-3 was obtained. (31.2 g, yield: 75%)

(4) Compound E-4

[Reaction Formula 4-4]

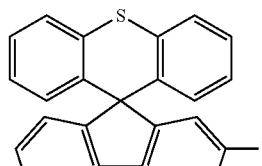

E-3

-continued

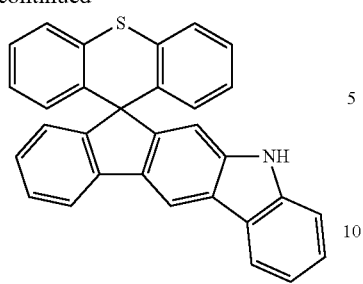

5H-spiro[indeno[2,1-b]carbazole-7,9'-thioxanthene]

E-4

In a two-neck flask (500 ml), the compound E-3 (31.2 g, 71.7 mmol) and Pd(OAc)₂ (0.8 g, 3.5 mmol) were suspended in acetic acid (230 ml), and the mixture was refluxed and stirred for 12 hrs. After completion of the reaction, the mixture was extracted with dichloromethane and distilled water, and the organic layer was removed under reduced-pressure distillation. The resultant was chromatographed using silica-gel such that the compound E-4 was obtained. (22.7 g, yield: 73%)

(5) Compound 1-6

[Reaction Formula 4-5]

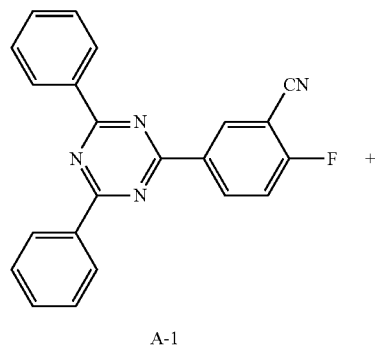

A-1

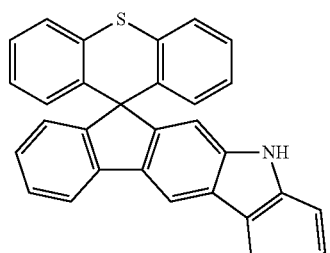

E-4

-continued

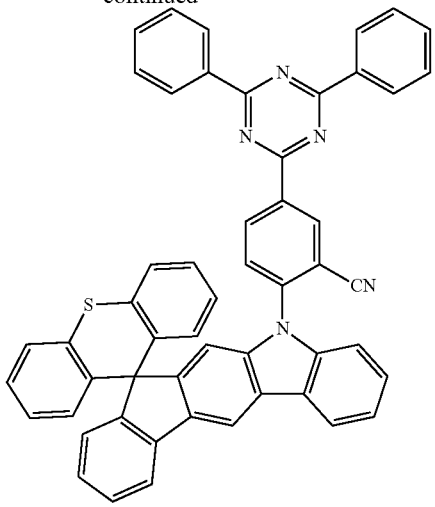

5-(4,6-diphenyl-1,3,5-triazin-2-yl)-2-(5H-spiro[indeno[2,1 b)carbazole-7,9'-thioxanthen]5-yl)benzonitrile In a two-neck flask (500 ml), the compound A-1 (3.5 g, 9.9 mmol), the compound E-4 (4.3 g, 9.9 mmol) and cesium carbonate (6.5 g, 19.9 mmol) were suspended in DMF (50 ml), and the mixture was stirred under a temperature of 190° C. for 16 hrs. After completion of the reaction, the mixture was extracted with dichloromethane and distilled water, and the organic layer was removed under reduced-pressure distillation. The resultant was chromatographed using silica-gel such that the compound 1-6 was obtained. (4.3 g, yield: 56%)

5. Synthesis of Compound 2-1

(1) Compound F-1

[Reaction Formula 5-1]

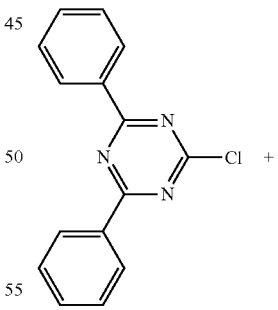

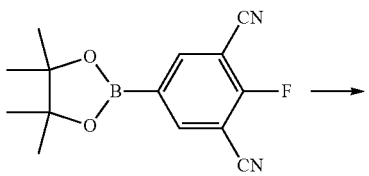

-continued

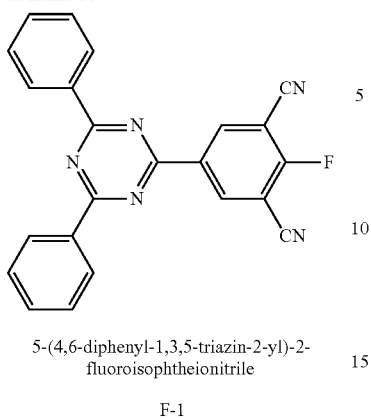

5-(4,6-diphenyl-1,3,5-triazin-2-yl)-2-fluoroisophtheionitrile

F-1

In a two-neck flask (500 ml), 2-chloro-4,6-diphenyl-1,3,5-triazine (10.0 g, 37.35 mmol), 2-fluoro-5-(4,4,5,5-tetramethyl-1,3,2-dioxaborolan-2-yl)isophthalonitrile (15.24 g, 56.03 mmol), $K_2CO_3$ (25.81 g, 186.77 mmol) and $Pd(PPh_3)_4$ (1.29 g, 1.12 mmol) were dissolved in a mixed solvent of THF and water (volume ratio=3:1, 200 ml). The mixture was refluxed and stirred for 12 hrs. After completion of the reaction, the mixture was chromatographed using MC and hexane (volume ratio=3:7) such that the compound F-1 of solid state was obtained. (10.0 g, yield: 75.98%)

(2) Compound 2-1

[Reaction Formula 5-2]

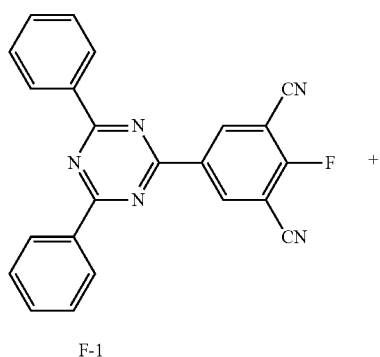

F-1

+

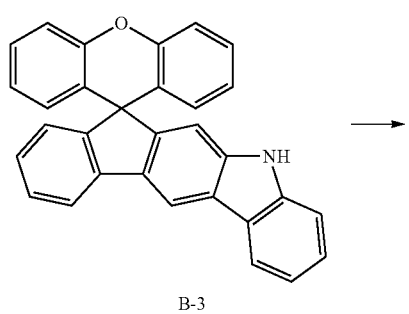

B-3

→

-continued

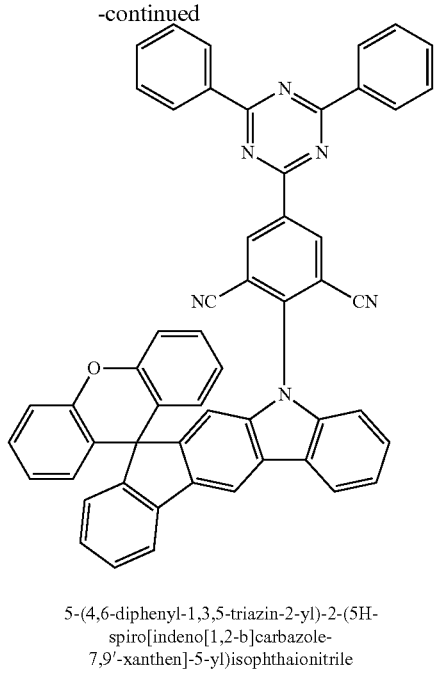

5-(4,6-diphenyl-1,3,5-triazin-2-yl)-2-(5H-spiro[indeno[1,2-b]carbazole-7,9'-xanthen]-5-yl)isophthaionitrile In a two-neck flask (500 ml), the compound F-1 (3.5 g, 9.27 mmol), the compound B-3 (4.3 g, 10.20 mmol) and cesium carbonate (6.04 g, 18.55 mmol) were suspended in DMF (50 ml), and the mixture was stirred under a temperature of 190° C. for 16 hrs. After completion of the reaction, the mixture was extracted with dichloromethane and distilled water, and the organic layer was removed under reduced-pressure distillation. The resultant was chromatographed using silica-gel such that the compound 2-1 was obtained. (4.0 g, yield: 55.37%)

Referring to FIG. 2, the EML 240 may further include a host. In the EML 240, the host may be present in a percentage by weight of approximately 50 to 99%, and the dopant (i.e., the delayed fluorescent compound of the present disclosure), may be present in a percentage by weight of about 1 to 50%. For example, the host may have a percentage by weight of approximately 60 to 80%, and the dopant may have a percentage by weight of about 20 to 40%.

The difference "|$HOMO_{Host}-HOMO_{Dopant}$|" between an energy level of the HOMO of the host "$HOMO_{Host}$" and an energy level of the HOMO of the dopant "$HOMO_{Dopant}$" or the difference "|$LUMO_{Host}-LUMO_{Dopant}$|" between an energy level of the LUMO of the host "$LUMO_{Host}$" and an energy level of the LUMO of the dopant "$LUMO_{Dopant}$" is less than about 0.5 eV. In this instance, the charge transfer efficiency from the host to the dopant may be improved.

The energy level of triplet state of the dopant is smaller than the energy level of triplet state of the host, and the difference between the energy level of singlet state of the dopant and the energy level of triplet state of the dopant is equal to less than 0.3 eV. ($\Delta E_{ST} \leq 0.3$ eV.) As the difference "$\Delta E_{ST}$" is smaller, the emitting efficiency is higher. In addition, even if the difference "$\Delta E_{ST}$" between the energy level of the singlet state of the dopant and the energy level of the triplet state of the dopant is about 0.3 eV, which is relatively large, the excitons in the singlet state ($S_1$) and the excitons in the triplet state ($T_1$) can be transited into the intermediate state.

In an exemplary embodiment, the host is selected from the compounds of Formula 3.

[Formula 3]

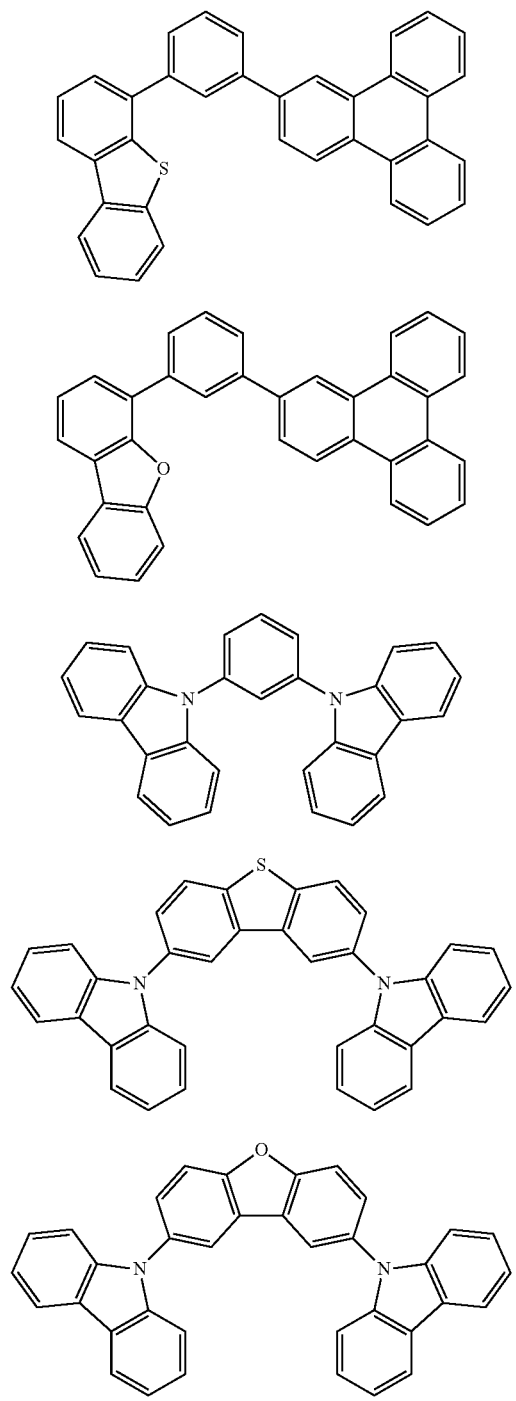

The EML 240 may include the delayed fluorescent compound of the present disclosure as a first dopant and a host with a second dopant. In the EML 240, the sum of the percentage by weight of the first and second dopants may be about 1 to 50. For example, the second dopant may be a fluorescent material (compound).

Since the EML 240 includes the host and the first and second dopants, the emitting efficiency may be improved by the first dopant and the color purity may be improved by the second dopant. Namely, after the triplet exciton in the first dopant, which has a high emitting efficiency, is converted into the singlet exciton in the first dopant, the singlet exciton in the first dopant is transferred into the second dopant, which has narrow full width at a half maximum (FWHM) such that the light emission is provided from the second dopant. As a result, the emitting efficiency and the color purity of the OLED D are improved.

An energy level of the singlet state of the first dopant (the delayed fluorescent compound) is greater than that of the second dopant (the fluorescent compound). An energy level of the triplet state of the first dopant is smaller than that of the host and greater than that of the second dopant.

As mentioned above, in the delayed fluorescent compound of the present disclosure, the triplet exciton is activated by an external force, e.g., an electric field generated in the operation of the OLED, such that the singlet exciton and the triplet exciton are involved in the light emission. Accordingly, the delayed fluorescent compound provides high emitting efficiency.

As a result, in the OLED D and the organic light emitting display device 100 including the delayed fluorescent compound, the emitting efficiency is improved, and a high quality image is provided.

[OLED]

The following layers are sequentially deposited on an ITO layer (anode).

(a) HIL (the compound of Formula 4 (HATCN), 7 nm), (b) HTL (the compound of Formula 5 (NPB), 55 nm), (c) EBL (the compound of Formula 6 (m-CBP), 10 nm), (d) EML (35 nm), (e) HBL (the compound of Formula 7 (B3PYMPM), 10 nm), (f) ETL (the compound of Formula 8 (TPBi), 20 nm), (g) EIL (LiF), and (h) Cathode (Al)

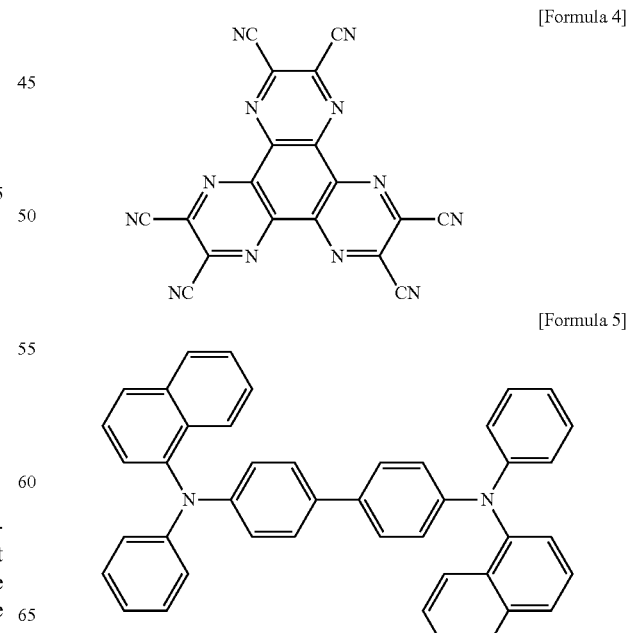

-continued

[Formula 6]

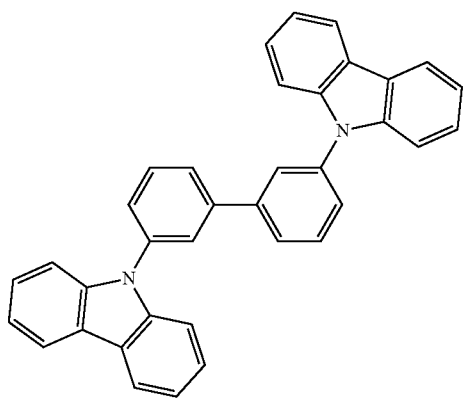

[Formula 7]

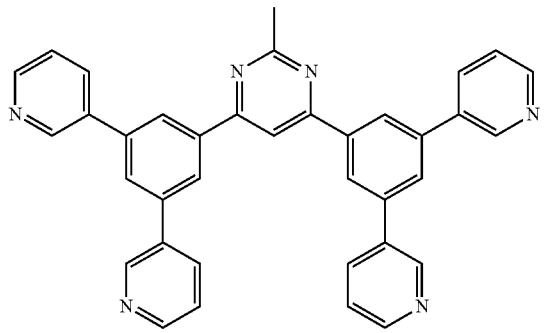

[Formula 8]

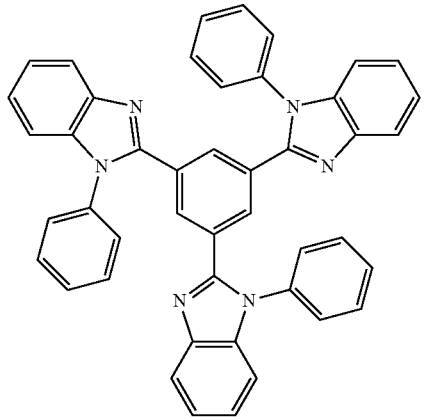

(1) Reference Example 1

In the EML, the compound H-1 of Formula 3 (70 wt %) is used as the host, and the compound of Formula 9 (30 wt %) is used as the delayed fluorescent dopant.

(2) Reference Example 2

In the EML, the compound H-1 of Formula 3 (70 wt %) is used as the host, and the compound of Formula 10 (30 wt %) is used as the delayed fluorescent dopant.

(3) Reference Example 3

In the EML, the compound H-1 of Formula 3 (70 wt %) is used as the host, and the compound of Formula 11 (30 wt %) is used as the delayed fluorescent dopant.

(4) Reference Example 4

In the EML, the compound H-1 of Formula 3 (70 wt %) is used as the host, and the compound of Formula 12 (30 wt %) is used as the delayed fluorescent dopant.

(5) Example 1

In the EML, the compound H-1 of Formula 3 (70 wt %) is used as the host, and the compound 1-1 of Formula 2 (30 wt %) is used as the delayed fluorescent dopant.

(6) Example 2

In the EML, the compound H-1 of Formula 3 (70 wt %) is used as the host, and the compound 1-2 of Formula 2 (30 wt %) is used as the delayed fluorescent dopant.

(7) Example 3

In the EML, the compound H-1 of Formula 3 (70 wt %) is used as the host, and the compound 1-3 of Formula 2 (30 wt %) is used as the delayed fluorescent dopant.

(8) Example 4

In the EML, the compound H-1 of Formula 3 (70 wt %) is used as the host, and the compound 1-6 of Formula 2 (30 wt %) is used as the delayed fluorescent dopant.

(9) Example 5

In the EML, the compound H-1 of Formula 3 (70 wt %) is used as the host, and the compound 2-1 of Formula 2 (30 wt %) is used as the delayed fluorescent dopant.

[Formula 9]

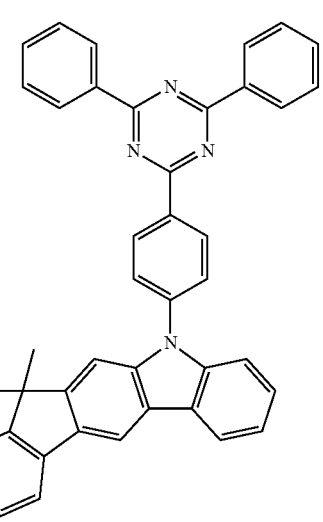

-continued

[Formula 10]

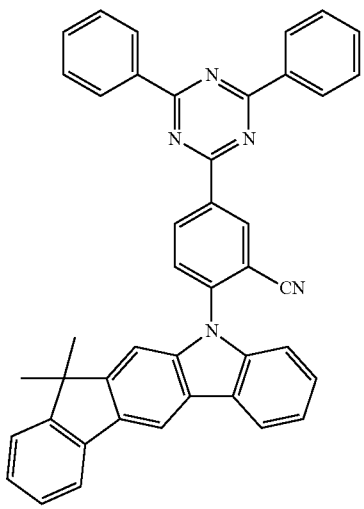

[Formula 11]

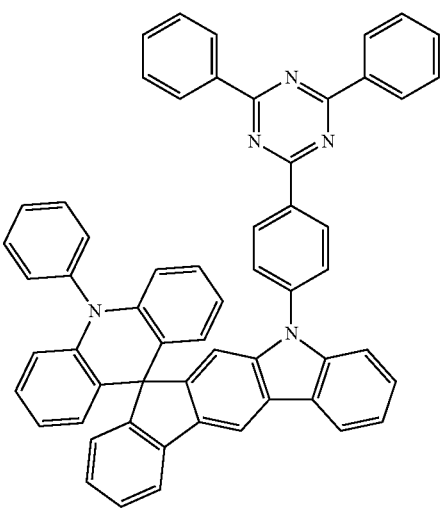

[Formula 12]

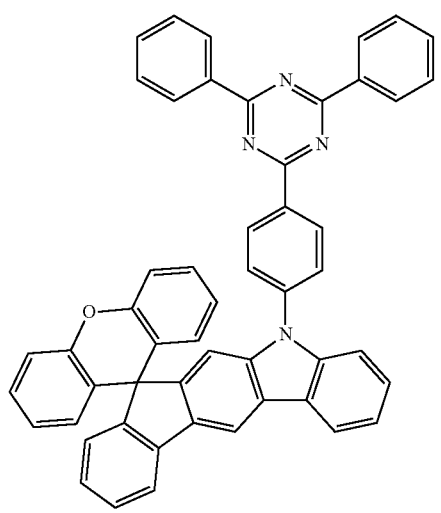

The properties of voltage (V), current efficiency (cd/A), power efficiency (lm/W), external quantum efficiency (EQE), maximum EL ($EL_{\lambda max}$), and CIE color coordinate of the OLED of the Reference Examples 1 to 4 and the Examples 1 to 5 are measured and listed in Table 1.

TABLE 1

|  | V | cd/A | lm/W | EQE (%) | $EL_{\lambda max}$ (nm) | CIE |
|---|---|---|---|---|---|---|
| Ref1 | 4.51 | 20.98 | 14.61 | 7.88 | 504 | (0.228, 0.446) |
| Ref2 | 4.16 | 41.31 | 31.20 | 13.59 | 516 | (0.275, 0.539) |
| Ref3 | 4.13 | 7.27 | 5.53 | 2.14 | 528 | (0.319, 0.594) |
| Ref4 | 3.90 | 9.84 | 7.92 | 3.59 | 510 | (0.261, 0.461) |
| Ex1 | 2.81 | 61.42 | 68.66 | 19.23 | 536 | (0.360, 0.569) |
| Ex2 | 3.55 | 54.51 | 48.28 | 17.18 | 523 | (0.333, 0.569) |
| Ex3 | 3.82 | 52.93 | 43.55 | 16.68 | 526 | (0.327, 0.569) |
| Ex4 | 3.93 | 58.37 | 46.66 | 18.09 | 536 | (0.341, 0.568) |
| Ex5 | 4.12 | 45.64 | 34.79 | 15.03 | 518 | (0.291, 0.546) |

As shown in Table 1, in comparison to the OLED in Reference Examples 1 to 4, the OLED of Examples 1 to 5 including the delayed fluorescent compound of the present disclosure exhibits a high emitting efficiency.

Particularly, in comparison to the OLED in Reference Example 4, the emitting efficiency of the OLED of Examples 1 and 5 respectively including the compound 1-1 and the compound 2-1, where the phenylene linker is substituted by cyano group, is significantly improved.

Figure 4:
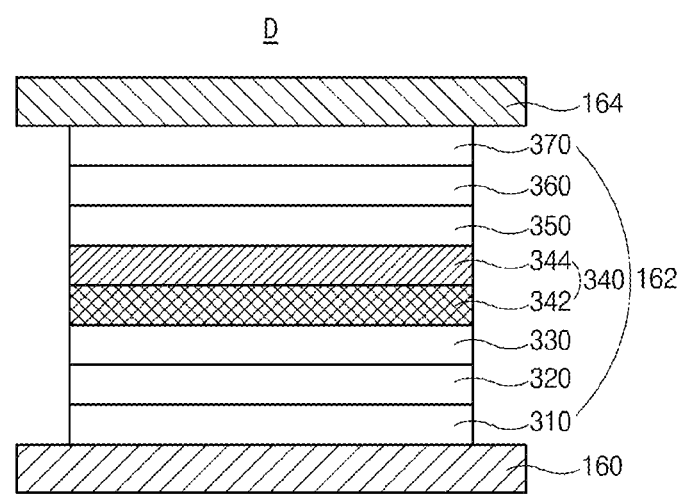
FIG. 4 is a schematic-cross sectional view of an OLED according to a second embodiment of the present disclosure.

FIG. 4 is a schematic-cross sectional view of an OLED according to a second embodiment of the present disclosure.

As shown in FIG. 4, an OLED D includes the first and second electrodes 160 and 164, which face each other, and the organic emitting layer 162 therebetween. The organic emitting layer 162 includes an EML 340, which includes first and second layers 342 and 344 and is positioned between the first and second electrodes 160 and 164, an HTL 320 between the first electrode 160 and the EML 340, and an ETL 360 between the second electrode 164 and the EML 340.

In addition, the organic emitting layer 162 may further include a HIL 310 between the first electrode 160 and the HTL 320, and an EIL 370 between the second electrode 164 and the ETL 360.

Moreover, the organic emitting layer 162 may further include an EBL 330 between the HTL 320 and the EML 340, and a HBL 350 between the EML 340 and the ETL 360.

For example, in the EML 340, one of the first layers 342 (e.g., a first emitting material layer) and the second layer 344 (e.g., a second emitting material layer) may include the delayed fluorescent compound of the present disclosure as a first dopant (a delayed fluorescent dopant). The other one of the first and second layers 342 and 344 may include a fluorescent compound as a second dopant (a fluorescent dopant). The energy level of the singlet state of the delayed fluorescent compound is higher than that of the fluorescent compound.

The OLED D, where the first layer 342 includes the delayed fluorescent compound, and the second layer 344 includes the fluorescent compound, will be explained.

In the OLED D, the energy level of singlet state and the energy level of triplet state of the delayed fluorescent compound are transferred into the fluorescent compound such that the light emission is provided from the fluorescent compound. As a result, the quantum efficiency of the OLED D is increased, and the FWHM of the OLED D is narrowed.

The delayed fluorescent compound having a delayed fluorescence property has high quantum efficiency. However, since the light emitted from the delayed fluorescent compound has wide FWHM, the light from the delayed fluorescent compound exhibits poor color purity. On the other hand, the fluorescence compound has a narrow FWHM and high color purity. However, since the energy level of triplet state of the fluorescence compound is not involved in the emission, the fluorescence compound has a low quantum efficiency.

Since the EML 340 of the OLED D in the present disclosure includes the first layer 342, which includes the delayed fluorescent compound as the dopant, and the second layer 344, which includes the fluorescence compound as the dopant, the OLED D exhibits advantages in both emitting efficiency and color purity.

The energy level of the triplet state of the delayed fluorescent compound is converted into the energy level of the singlet state of the delayed fluorescent compound by the reverse intersystem crossing (RISC) effect, and the energy level of the singlet state of the delayed fluorescent compound is transferred into the energy level of the singlet state of the fluorescence compound. Namely, the difference between the energy level of the triplet state of the delayed fluorescent compound and the energy level of the singlet state of the delayed fluorescent compound is not greater than 0.3 eV such that the energy level of the triplet state of the delayed fluorescent compound is converted into the energy level of the singlet state of the delayed fluorescent compound by the RISC effect.

As a result, the delayed fluorescent compound has an energy transfer function, and the first layer 342 including the delayed fluorescent compound is not involved in light emission. Instead, the light emission is generated in the second layer 344 including the fluorescence compound.

The energy level of the triplet state of the delayed fluorescent compound is converted into the energy level of the singlet state of the delayed fluorescent compound by the RISC effect. In addition, since the energy level of the singlet state of the delayed fluorescent compound is higher than that of the fluorescence compound, the energy level of the singlet state of the delayed fluorescent compound is transferred into the energy level of the singlet state of the fluorescence compound. As a result, the fluorescence compound emits light using the energy level of the singlet state and the energy level of the triplet state such that the quantum efficiency (emitting efficiency) of the OLED D is improved.

In other words, the OLED D and the organic light emitting display device 100 (of FIG. 1) including the OLED D exhibits advantages in both emitting efficiency (quantum efficiency) and color purity (FWHM).

The first and second layers 342 and 344 may further include first and second hosts, respectively. The first and second hosts are the same material or different materials. Each of the first and second hosts may be selected from the materials of Formula 3. Alternatively, the first host may be selected from the materials of Formula 3, while the second host may be a common host compound.

The first and second hosts may have a larger percentage by weight than the delayed fluorescent compound and the fluorescence compound, respectively. In addition, the percentage by weight of the delayed fluorescent compound in the first layer 342 may be greater than that of the fluorescence compound in the second layer 344. As a result, the energy transfer from the delayed fluorescent compound into the fluorescence compound is sufficiently generated.

The energy level of the singlet state of the first host is greater than that of the delayed fluorescent compound (first dopant), and the energy level of the triplet state of the first host is greater than that of the delayed fluorescent compound. In addition, the energy level of the singlet state of the second host is greater than that of the fluorescence compound (second dopant).

When this condition is not satisfied, quenching occurs at the first and second dopants or there is no energy transfer from the host to the dopant, and thus the quantum efficiency of the OLED D is reduced.

For example, the second host, which is included in the second layer 344 with the fluorescence compound, may be the same as a material of the HBL 350. In this instance, the second layer 344 may have a hole blocking function with an emission function. Namely, the second layer 344 may serve as a buffer layer for blocking the hole. When the HBL 350 is omitted, the second layer 344 serves as an emitting layer and a hole blocking layer.

When the first layer 342 includes the fluorescence compound and the second layer 344 includes the delayed fluorescent compound, the first host of the first layer 342 may be same as a material of the EBL 330. In this instance, the first layer 342 may have an electron blocking function with an emission function. Namely, the first layer 342 may serve as a buffer layer for blocking the electron. When the EBL 330 is omitted, the first layer 342 serves as an emitting layer and an electron blocking layer.

Figure 5:
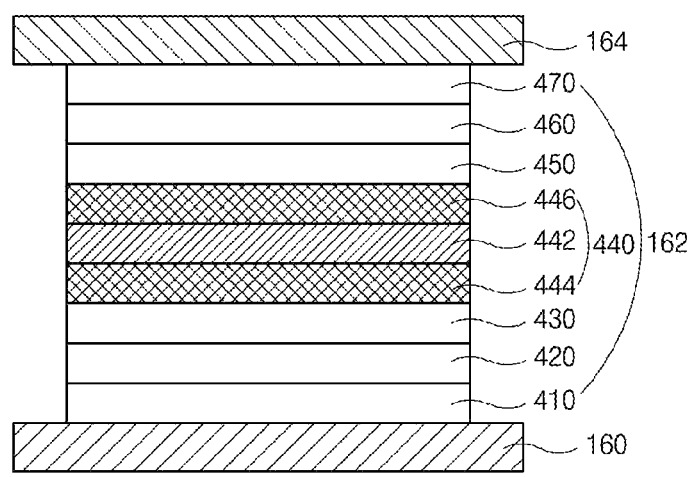
FIG. 5 is a schematic-cross sectional view of an OLED according to a third embodiment of the present disclosure.

FIG. 5 is a schematic-cross sectional view of an OLED according to a third embodiment of the present disclosure.

As shown in FIG. 5, an OLED D includes the first and second electrodes 160 and 164, which face each other, and the organic emitting layer 162 therebetween. The organic emitting layer 162 includes an EML 440, which includes first to third layers 442, 444 and 446 and is positioned between the first and second electrodes 160 and 164, a HTL 420 between the first electrode 160 and the EMIL 440, and an ETL 460 between the second electrode 164 and the EML 440.

In addition, the organic emitting layer 162 may further include a HIL 410 between the first electrode 160 and the HTL 420, and an EIL 470 between the second electrode 164 and the ETL 460.

Moreover, the organic emitting layer 162 may further include an EBL 430 between the HTL 420 and the EML 440, and a HBL 450 between the EML 440 and the ETL 460.

In the EML 440, the first layer 442 is positioned between the second layer 444 and the third layer 446. Namely, the second layer 444 is positioned between the EBL 430 and the first layer 442, and the third layer 446 is positioned between the first layer 442 and the HBL 450.

The first layer 442 (e.g., a first emitting material layer) includes the delayed fluorescent compound of the present disclosure as a dopant (a delayed fluorescent dopant), and each of the second layer 344 (e.g., a second emitting material layer) and the third layer 446 (e.g., a third emitting material layer) may include the fluorescence compound as a dopant (first and second fluorescent dopants). The fluorescence compound in the second and third layers 444 and 446 may be the same or different. The delayed fluorescent compound has an energy level of the singlet state being larger than the fluorescence material.

In the OLED D, the energy level of the singlet state and the energy level of the triplet state of the delayed fluorescent compound in the first layer 442 are transferred into the fluorescence compound in the second layer 444 and/or the third layer 446 such that the emission is generated from the fluorescence compound. As a result, the quantum efficiency of the OLED D is increased, and the FWHM of the OLED D is narrowed.

The first to third layers 442, 444 and 446 may further include a first to third host, respectively. The first to third hosts are the same material or different materials. Each of the first to third hosts may be selected from the materials of Formula 3. Alternatively, the first host may be selected from the materials of Formula 3, while each of the second and third hosts may be a common host compound.

In each of the first to third layers 442, 444 and 446, the first to third hosts may be present in a weight percentage larger than the delayed fluorescent compound and the fluorescence compound, respectively. In addition, the weight percentage of the delayed fluorescent compound (i.e., the first dopant) in the first layer 442 may be greater than that of each of the fluorescence compound (i.e., the second dopant) in the second layer 444 and the fluorescence compound (i.e., the third dopant) in the third layer 446.

The energy level of the singlet state of the first host is greater than that of the delayed fluorescent compound (i.e., the first dopant), and the energy level of the triplet state of the first host is greater than that of the delayed fluorescent compound. In addition, the energy level of the singlet state of the second host is greater than that of the fluorescence compound (i.e., the second dopant) in the second layer 444, and the energy level of the singlet state of the third host is greater than that of the fluorescence compound (i.e., the third dopant) in the third layer 446.

For example, the second host in the second layer 444 may be the same as a material of the EBL 430. In this instance, the second layer 444 may have an electron blocking function with an emission function. Namely, the second layer 444 may serve as a buffer layer for blocking the electron. When the EBL 430 is omitted, the second layer 444 serves as an emitting layer and an electron blocking layer.

The third host in the third layer 446 may be the same as a material of the HBL 450. In this instance, the third layer 446 may have a hole blocking function with an emission function. Namely, the third layer 446 may serve as a buffer layer for blocking the hole. When the HBL 450 is omitted, the third layer 446 serves as an emitting layer and a hole blocking layer.

The second host in the second layer 444 may be the same as a material of the EBL 430, and the third host in the third layer 446 may be the same as a material of the HBL 450. In this instance, the second layer 444 may have an electron blocking function with an emission function, and the third layer 446 may have a hole blocking function with an emission function. Namely, the second layer 444 may serve as a buffer layer for blocking the electron, and the third layer 446 may serve as a buffer layer for blocking the hole. When the EBL 430 and the HBL 450 are omitted, the second layer 444 serves as an emitting layer and an electron blocking layer and the third layer 446 serves as an emitting layer and a hole blocking layer.

It will be apparent to those skilled in the art that various modifications and variations can be made in the present disclosure without departing from the spirit or scope of the present disclosure. Thus, it is intended that the present disclosure cover the modifications and variations of the present disclosure provided they come within the scope of the appended claims and their equivalents.

What is claimed is:

1. A delayed fluorescent compound of Formula:

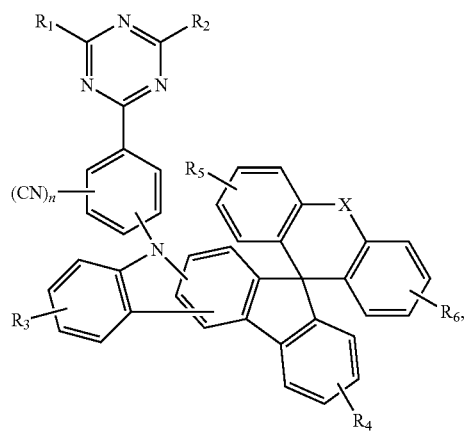

wherein

X is oxygen (O) or sulfur (S);

each of $R_1$ to $R_6$ is independently selected from the group consisting of hydrogen, a C1 to C20 alkyl group, a C1 to C20 alkoxy group, a C6 to C30 aryl group, a C5 to C30 heteroaryl group and a C1 to C20 amine group; and n is 1.

2. The delayed fluorescent compound according to claim 1, wherein the delayed fluorescent compound is one of the following compounds selected from:

compound 1-1

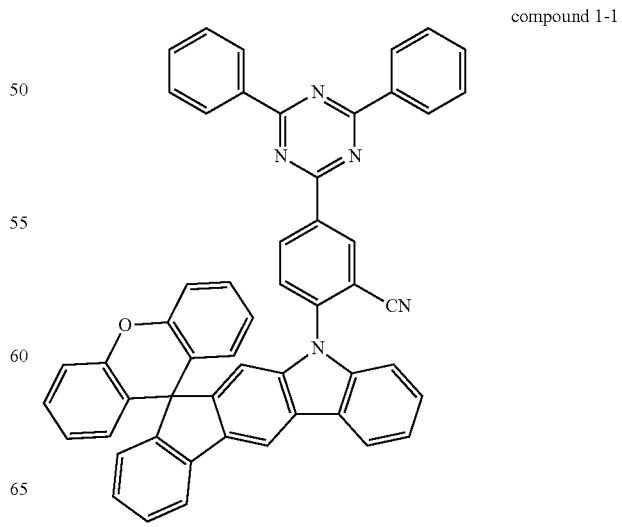

compound 1-2
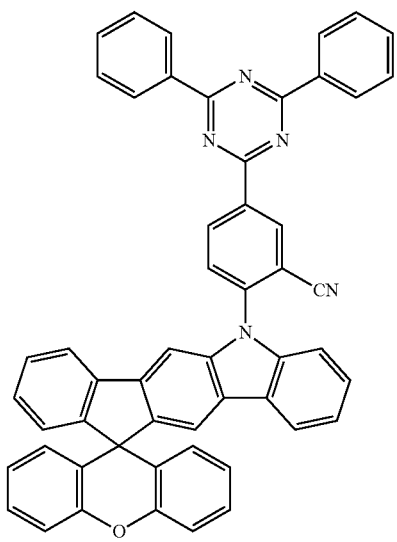
compound 1-3
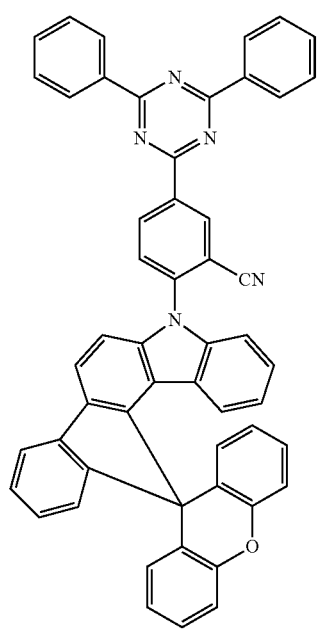
compound 1-4
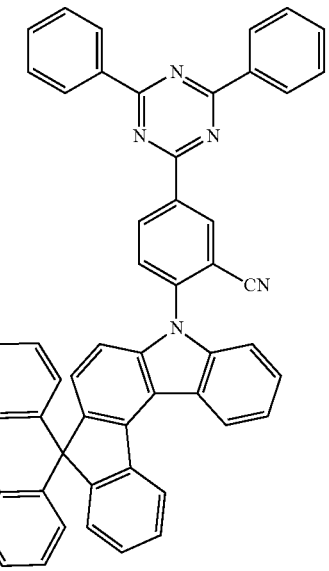
compound 1-5
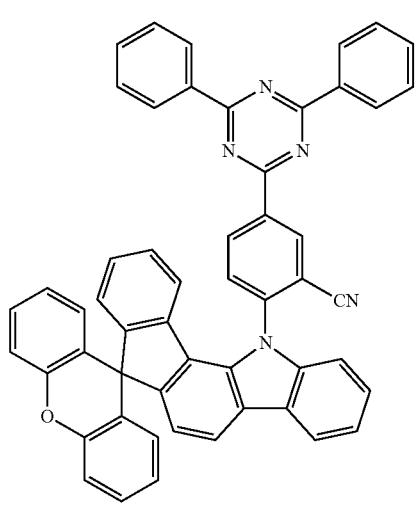
compound 1-6
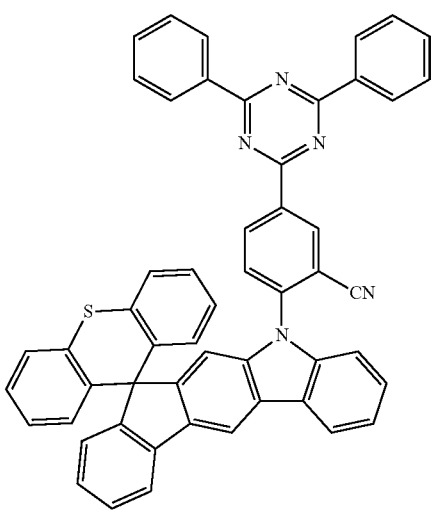

compound 1-7
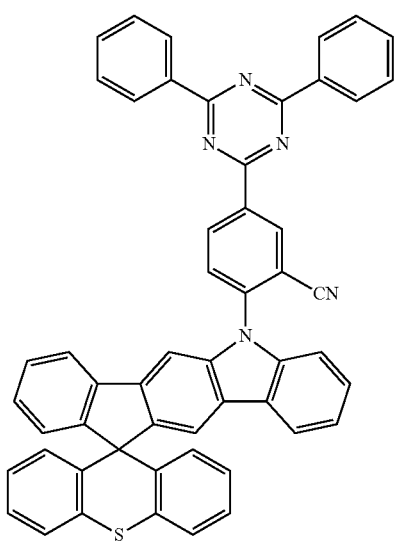
compound 1-9
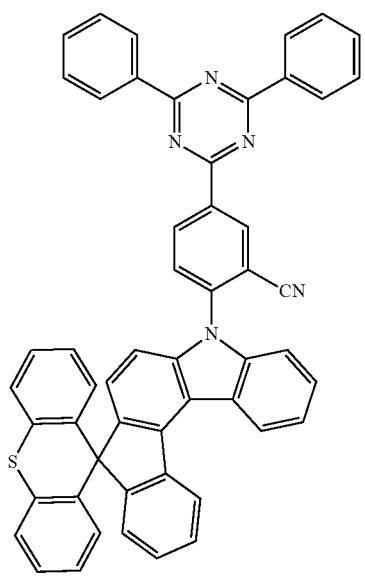
compound 1-8
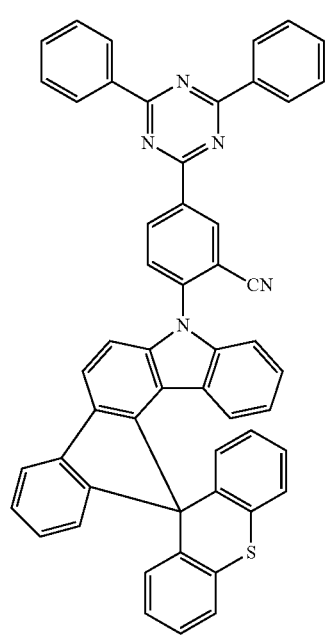
compound 1-10
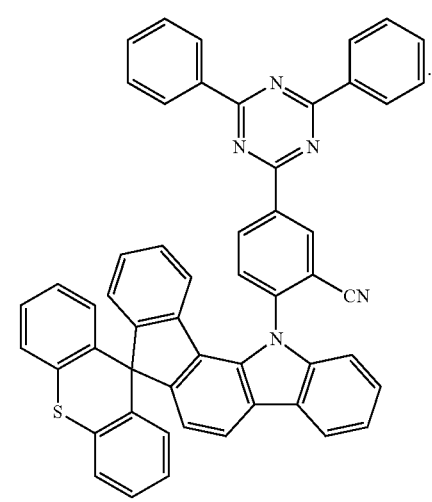
3. An organic light emitting diode, comprising:
 a first electrode;
 a second electrode facing the first electrode; and
 a first emitting material layer positioned between the first and second electrodes and including a delayed fluorescent compound, wherein the delayed fluorescent compound is represented by Formula:

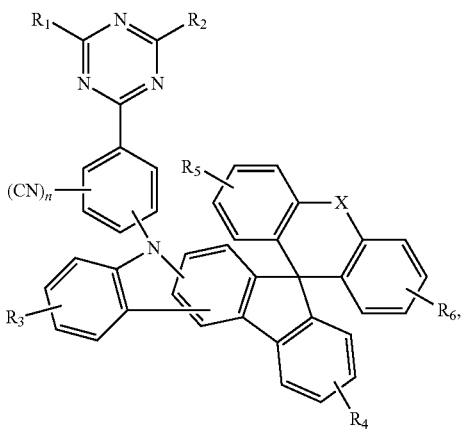

wherein
X is oxygen (O) or sulfur (S);
each of $R_1$ to $R_6$ is independently selected from the group consisting of hydrogen, a C1 to C20 alkyl group, a C1 to C20 alkoxy group, a C6 to C30 aryl group, a C5 to C30 heteroaryl group and a C1 to C20 amine group; and
n is an integer of 1 to 4, and
wherein the delayed fluorescent compound is a first dopant, and the first emitting material layer further includes a first host.

4. An organic light emitting display device, comprising:
a substrate; and
an organic light emitting diode on the substrate, the organic light emitting diode including:
a first electrode;
a second electrode facing the first electrode; and
a first emitting material layer positioned between the first and second electrodes and including a delayed fluorescent compound,
wherein the delayed fluorescent compound is represented by Formula:

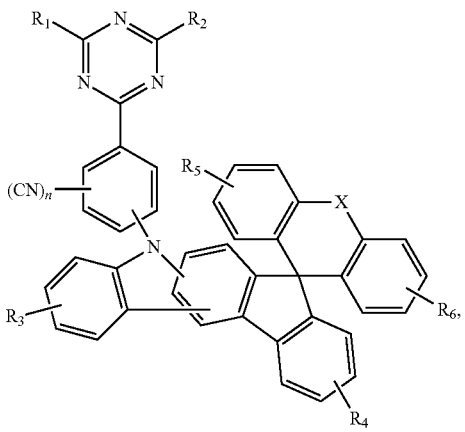

wherein
X is oxygen (O) or sulfur (S);
each of $R_1$ to $R_6$ is independently selected from the group consisting of hydrogen, a C1 to C20 alkyl group, a C1 to C20 alkoxy group, a C6 to C30 aryl group, a C5 to C30 heteroaryl group and a C1 to C20 amine group; and
n is an integer of 1 to 4, and
wherein the delayed fluorescent compound is a first dopant, and the first emitting material layer further includes a first host.

5. The organic light emitting diode according to claim 3, wherein there is a difference of less than about 0.5 eV between an energy level of a highest occupied molecular orbital (HOMO) of the first host and an energy level of a HOMO of the first dopant, or between an energy level of a lowest unoccupied molecular orbital (LUMO) of the first host and an energy level of a LUMO of the first dopant.

6. The organic light emitting diode according to claim 3, wherein the first host is selected from the group consisting of:

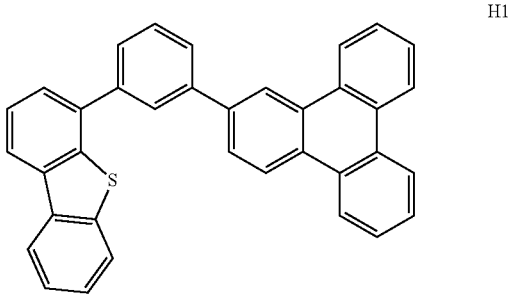

H1

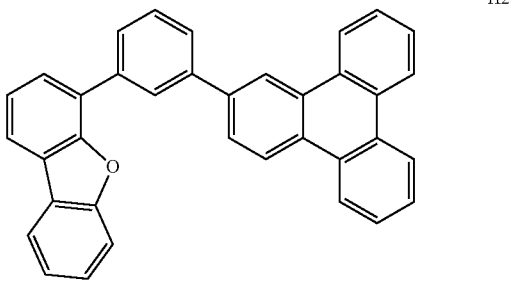

H2

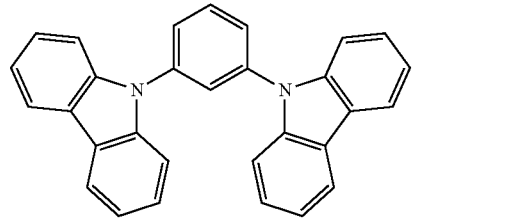

H3

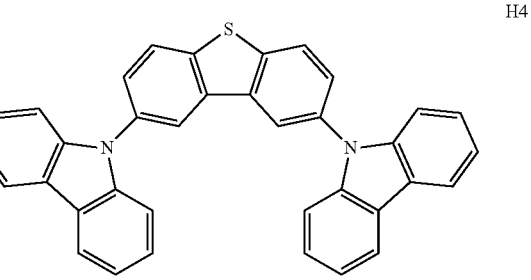

H4

-continued

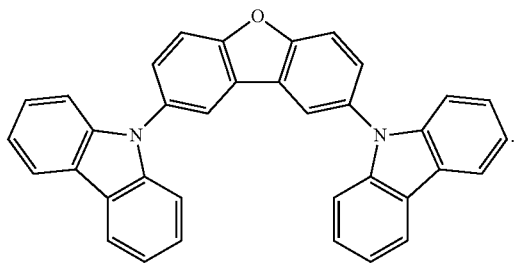
H5

7. The organic light emitting diode according to claim 3, wherein the first emitting material layer further includes a second dopant, and
wherein an energy level of a singlet state of the first dopant is greater than an energy level of a singlet state of the second dopant.

8. The organic light emitting diode according to claim 7, wherein an energy level of a triplet state of the first dopant is smaller than an energy level of a triplet state of the first host and greater than an energy level of a triplet state of the second dopant.

9. The organic light emitting diode according to claim 3, further comprising a second emitting material layer positioned between the first emitting material layer and the first electrode and including a second host and a first fluorescent dopant.

10. The organic light emitting diode according to claim 9, further comprising:
an electron blocking layer between the first electrode and the second emitting material layer,
wherein the second host is the same as a material of the electron blocking layer.

11. The organic light emitting diode according to claim 9, further comprising a third emitting material layer positioned between the first emitting material layer and the second electrode and including a third host and a second fluorescent dopant.

12. The organic light emitting diode according to claim 11, further comprising:
a hole blocking layer between the second electrode and the third emitting material layer,
wherein the third host is the same as a material of the hole blocking layer.

13. The organic light emitting diode according to claim 11, wherein an energy level of a singlet state of the first dopant is greater than each of an energy level of a singlet state of the first fluorescent dopant and an energy level of a singlet state of the second fluorescent dopant.

14. The organic light emitting diode according to claim 11,
wherein an energy level of a singlet state and an energy level of a triplet state of the first host is greater than an energy level of a singlet state and an energy level of a triplet state of the first dopant, respectively, and
wherein an energy level of a singlet state of the second host is greater than an energy level of a singlet state of the first fluorescent dopant, and an energy level of a singlet state of the third host is greater than an energy level of a singlet state of the second fluorescent dopant.

15. The organic light emitting diode according to claim 9, wherein an energy level of a singlet state of the first dopant is greater than an energy level of a singlet state of the first fluorescent dopant.

16. The organic light emitting diode according to claim 9,
wherein an energy level of a singlet state and an energy level of a triplet state of the first host are greater than an energy level of a singlet state and an energy level of a triplet state of the first dopant, respectively, and
wherein an energy level of a singlet state of the second host is greater than an energy level of a singlet state of the first fluorescent dopant.

17. The organic light emitting diode according to claim 3, wherein the delayed fluorescent compound is one of the following compounds selected from:

compound 1-1

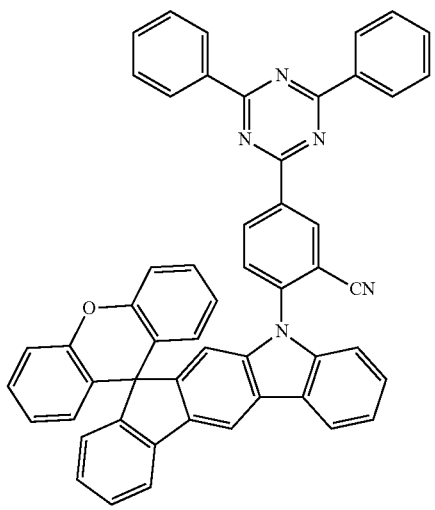

compound 1-2

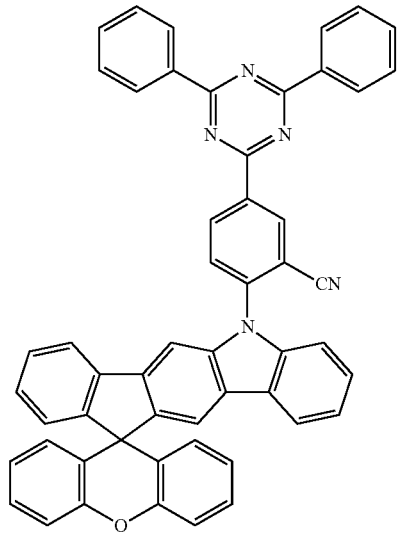

compound 1-3
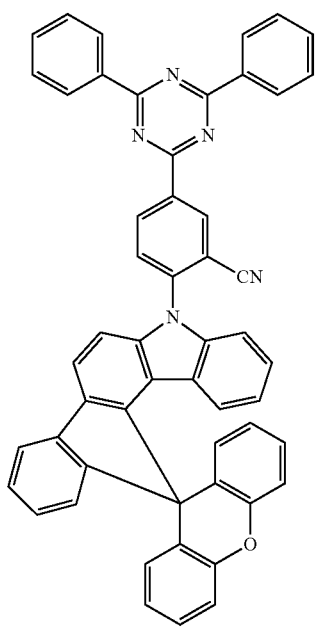
compound 1-4
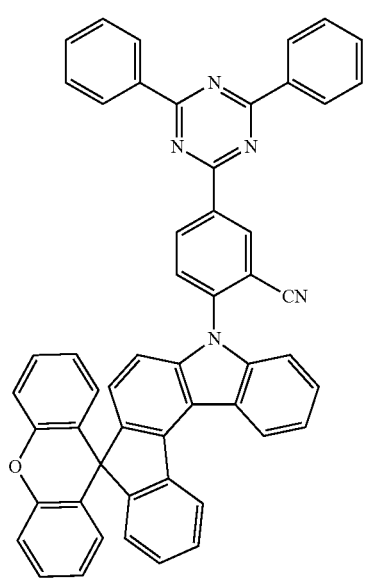
compound 1-5
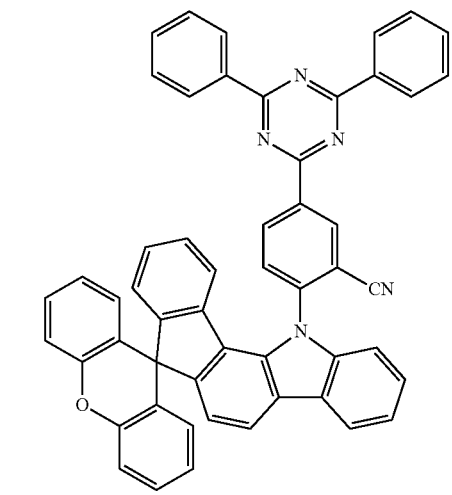
compound 1-6
compound 1-7
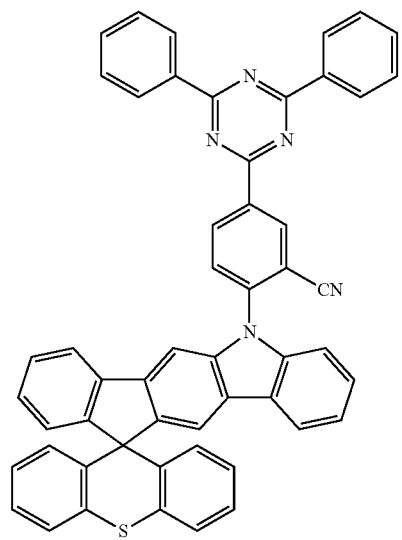

compound 1-8
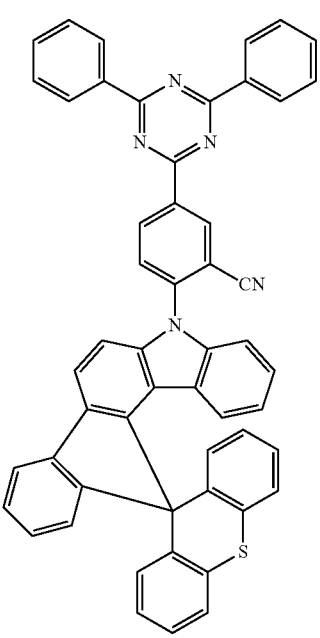
compound 1-10
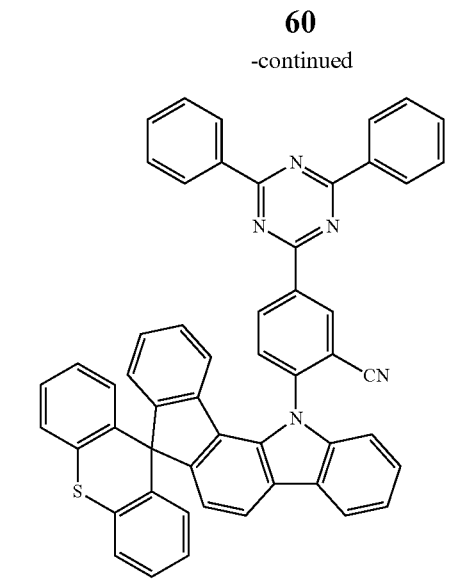
compound 2-1
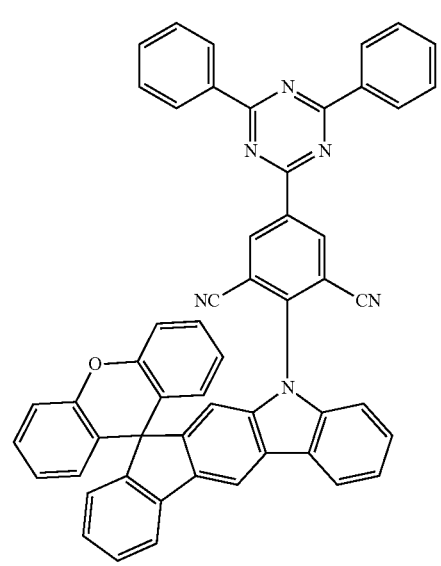
compound 1-9
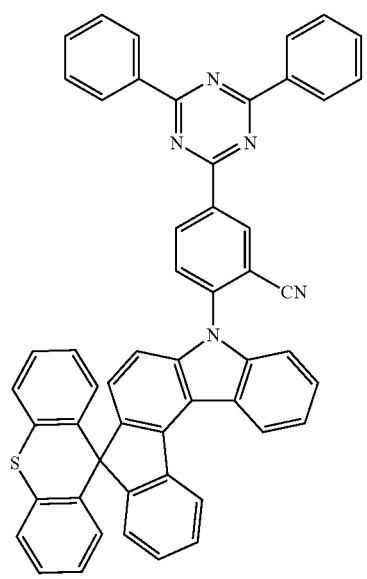
compound 2-2
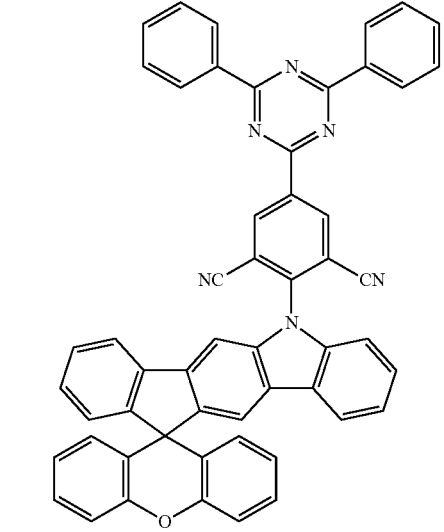

compound 2-3
compound 2-4
compound 2-5
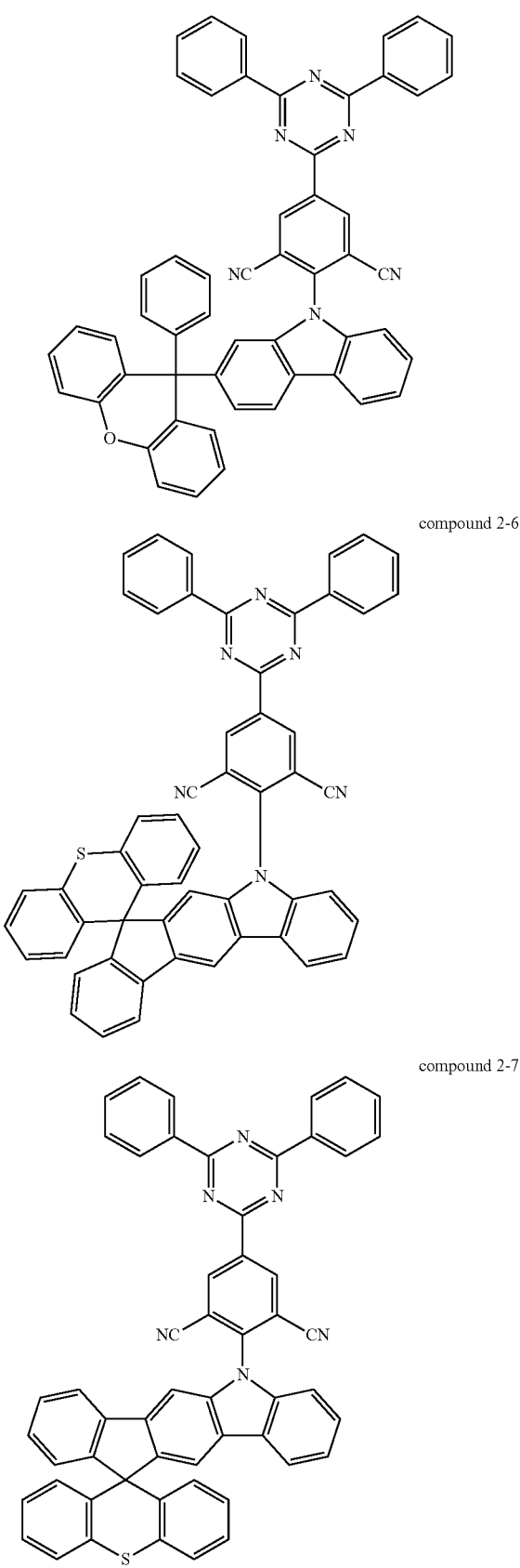
compound 2-6
compound 2-7 compound 2-8
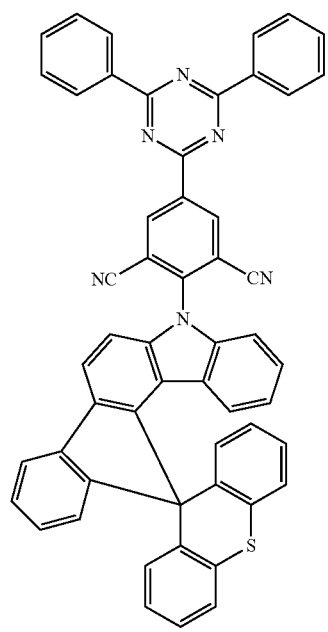
compound 2-9
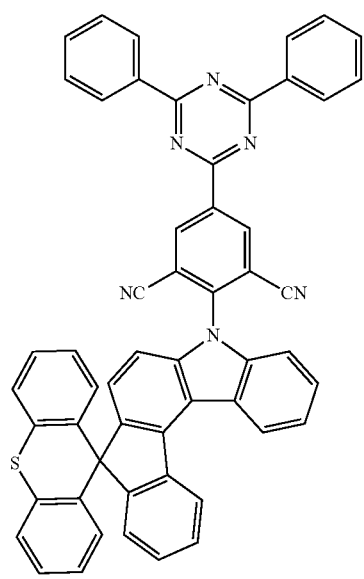
compound 2-10
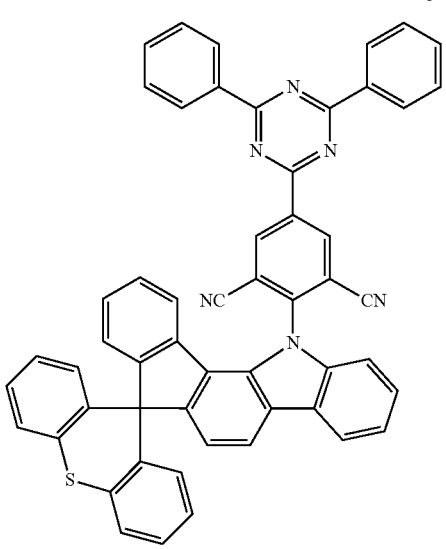
compound 3-1
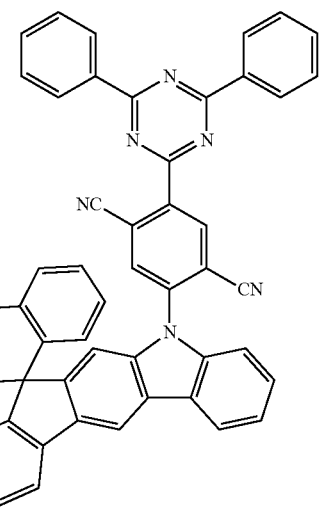
compound 3-2 compound 3-3
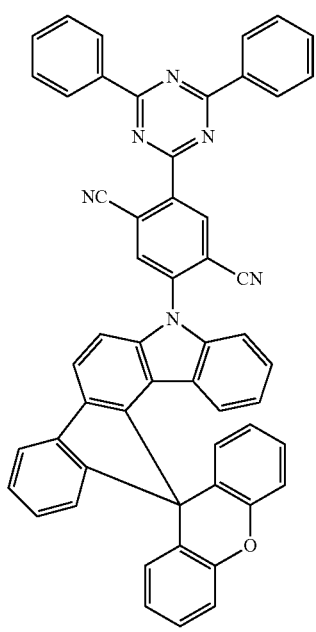
compound 3-5
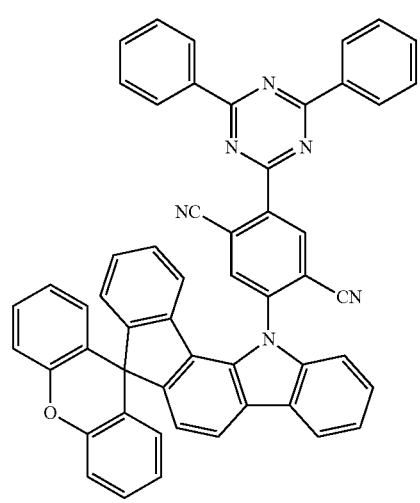
compound 3-6
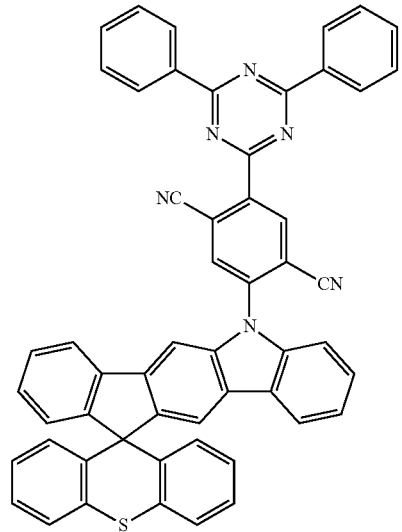
compound 3-4
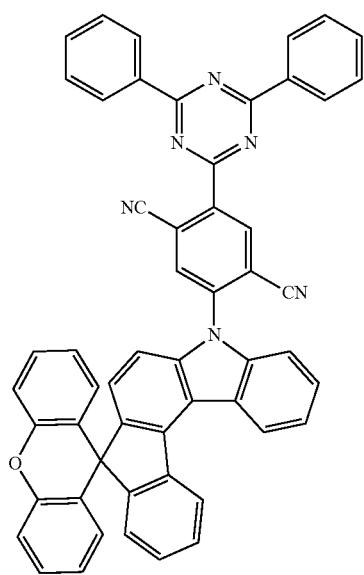
compound 3-7 compound 3-8
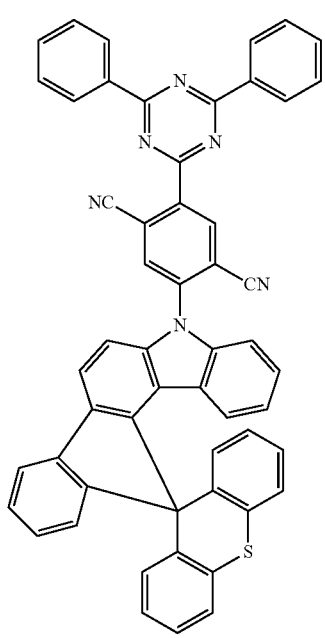
compound 3-10
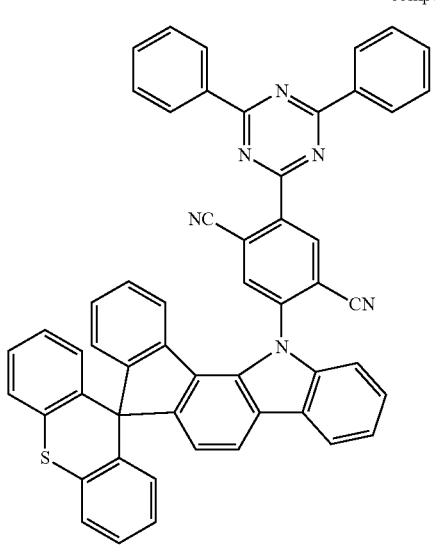
compound 4-1
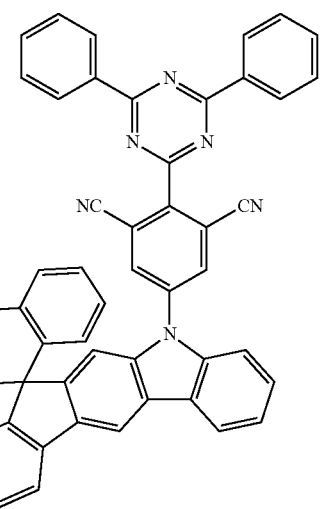
compound 3-9
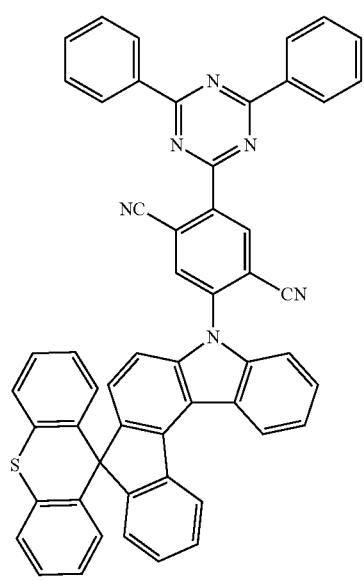
compound 4-2
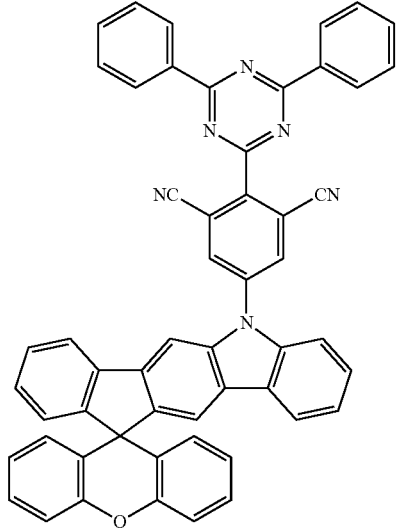

compound 4-3
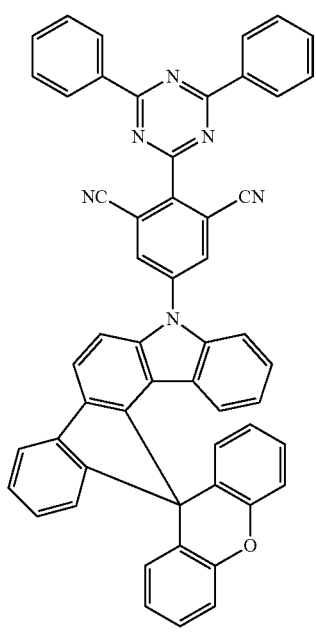
compound 4-4
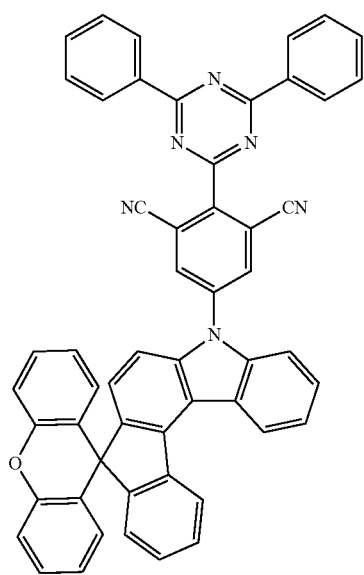
compound 4-5
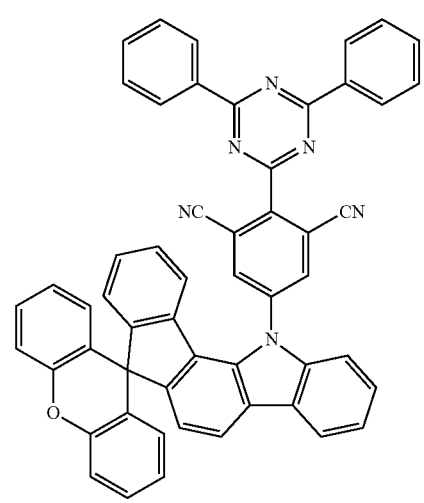
compound 4-6
compound 4-7
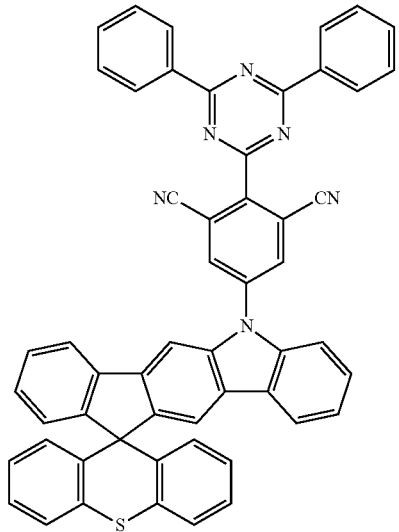

compound 4-8
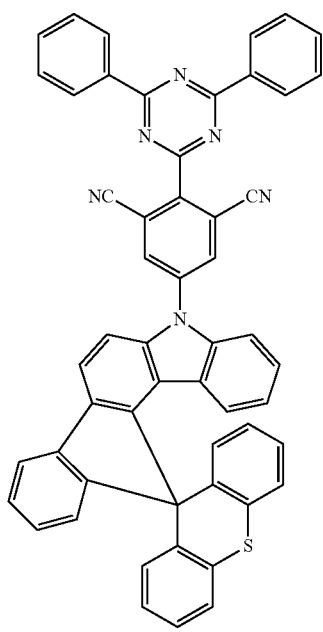
compound 4-10
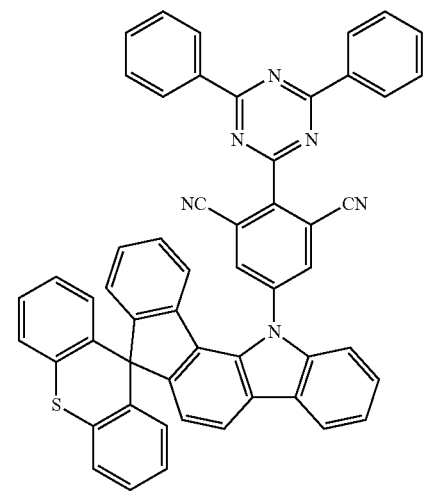
18. The organic light emitting display device according to claim 4, wherein the delayed fluorescent compound is one of the following compounds selected from:
compound 4-9
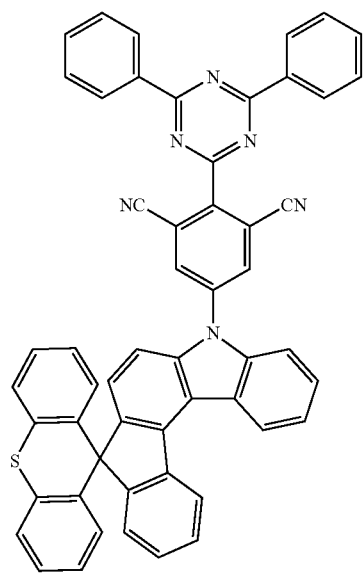
compound 1-1
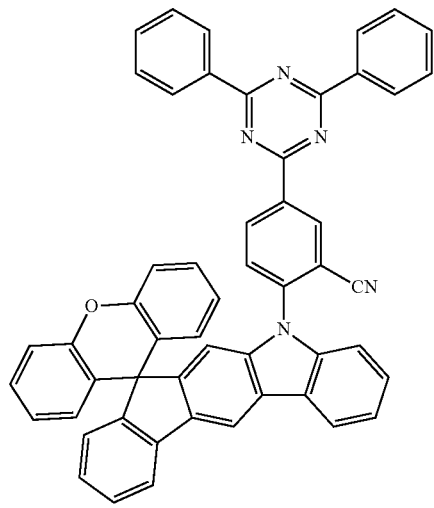

-continued
compound 1-2
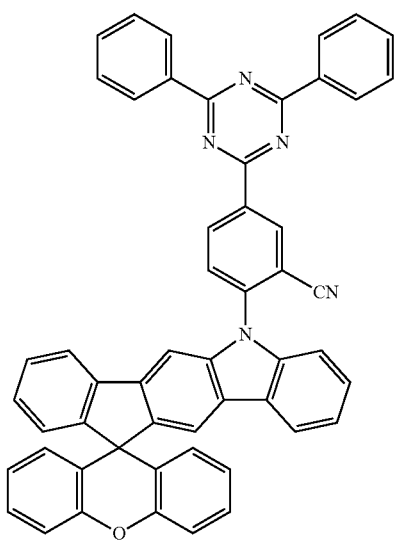
compound 1-3
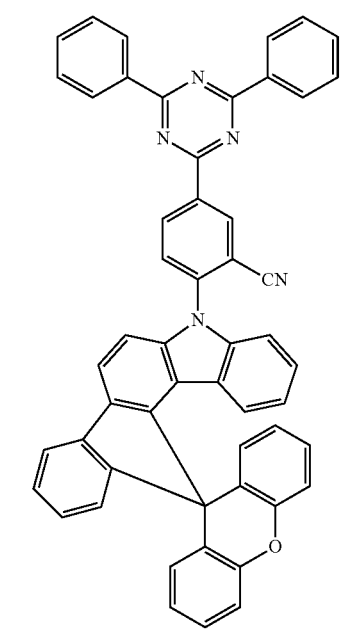
-continued
compound 1-4
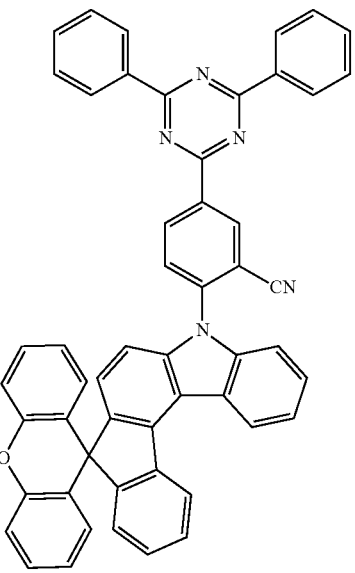
compound 1-5
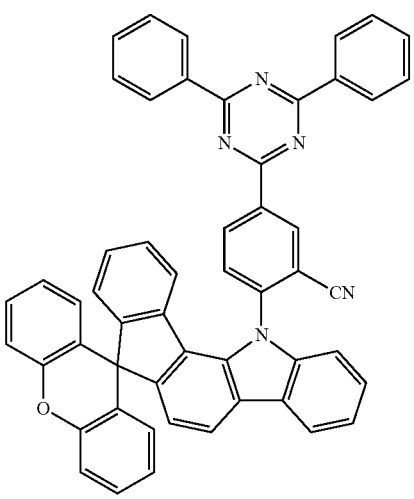
compound 1-6
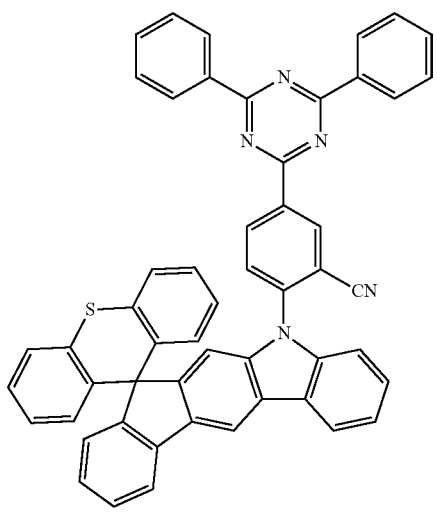

compound 1-7
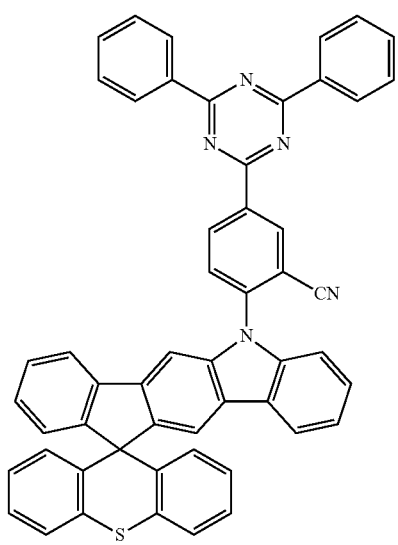
compound 1-9
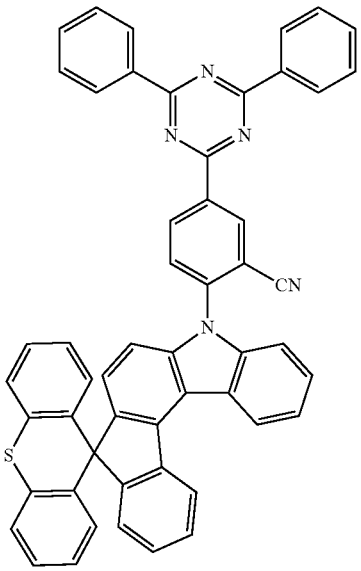
compound 1-10
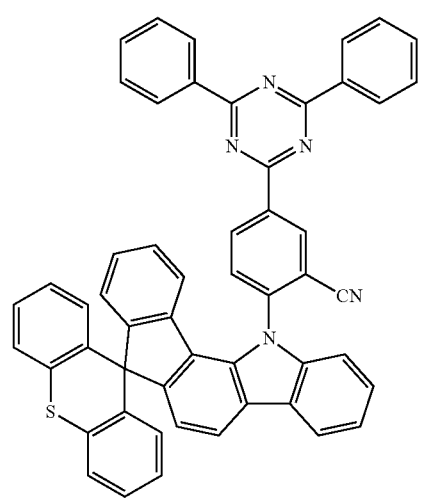
compound 1-8
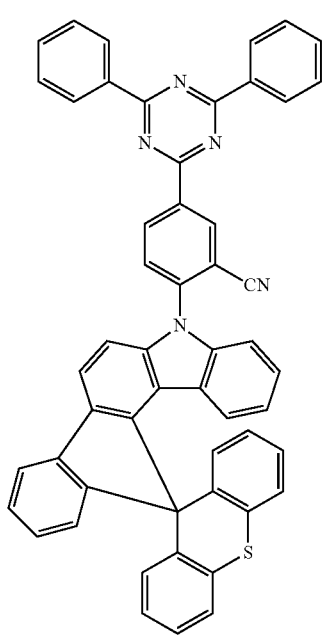
compound 2-1
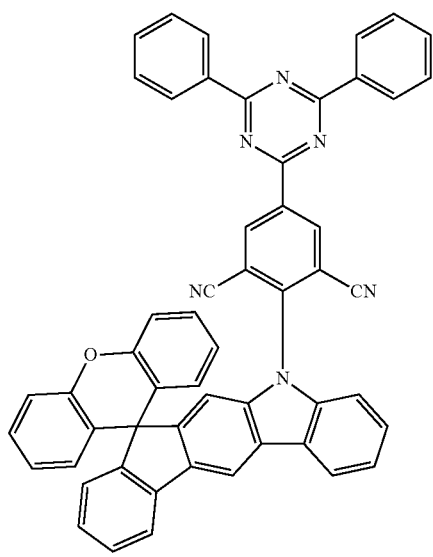

compound 2-2
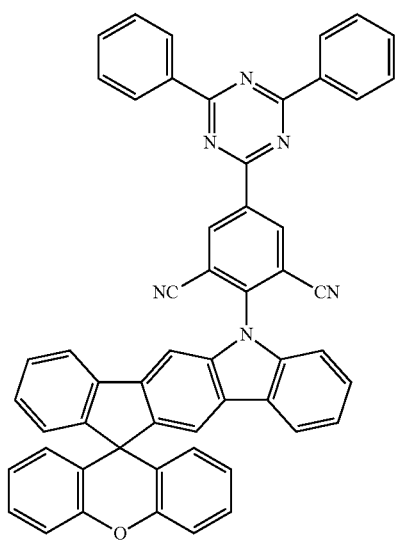
compound 2-4
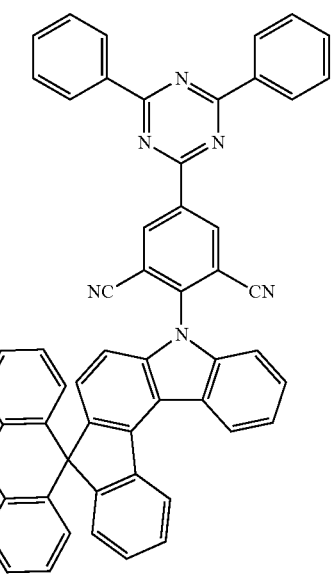
compound 2-5
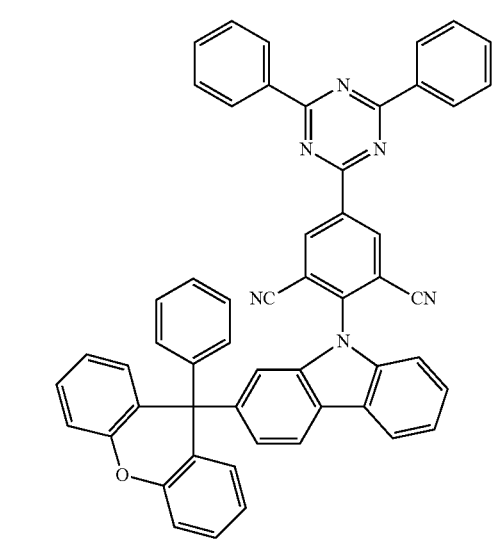
compound 2-3
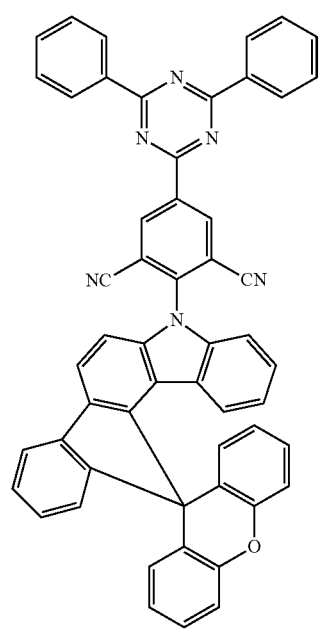
compound 2-6
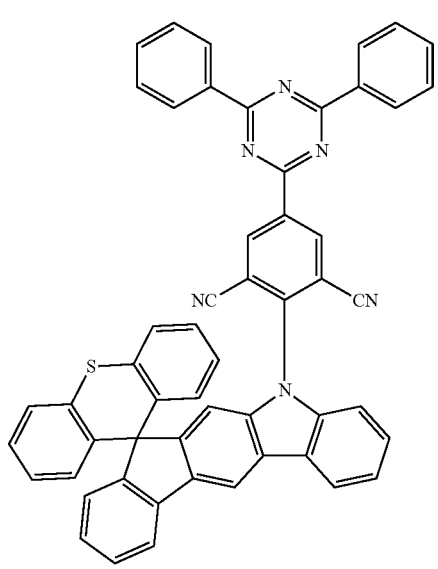

compound 2-7
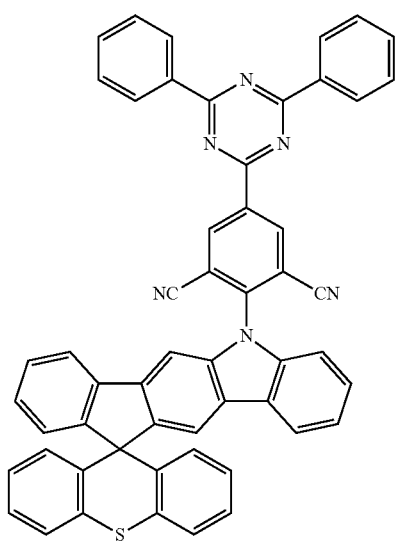
compound 2-8
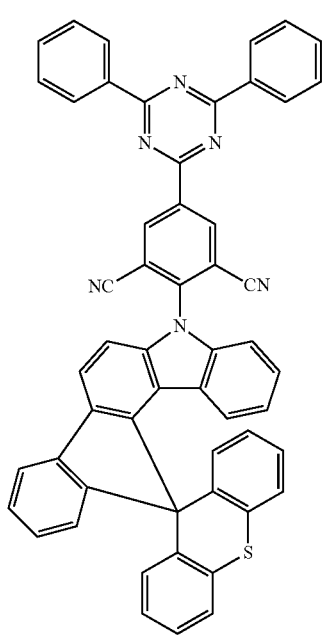
compound 2-9
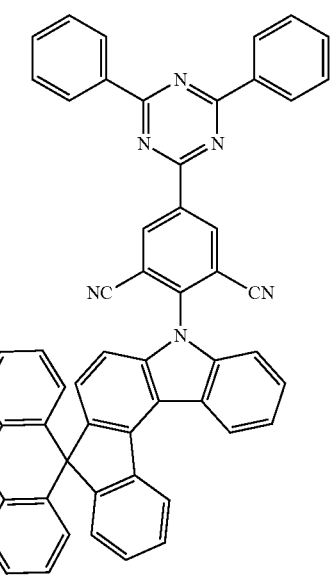
compound 2-10
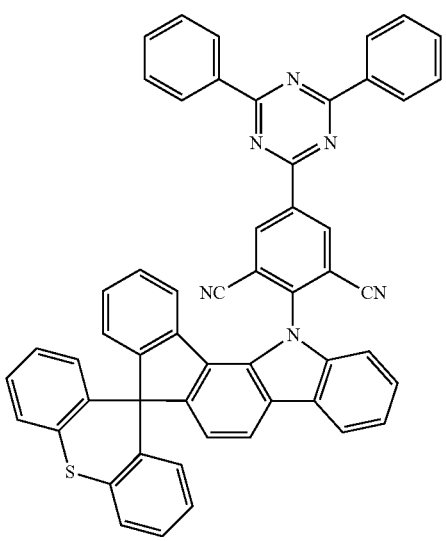
compound 3-1
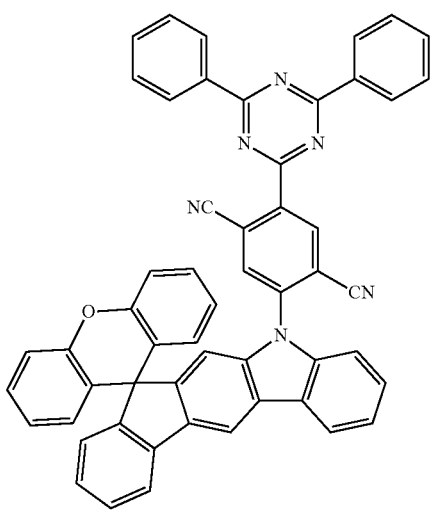

compound 3-2
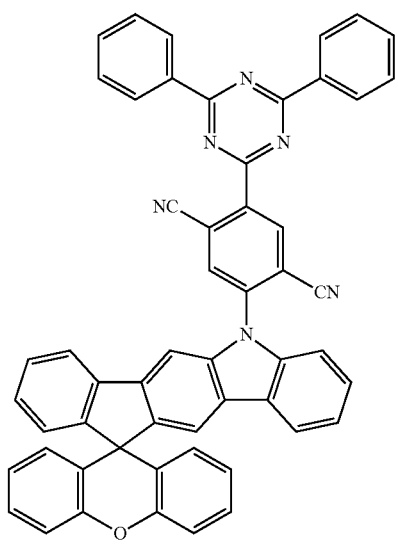
compound 3-4
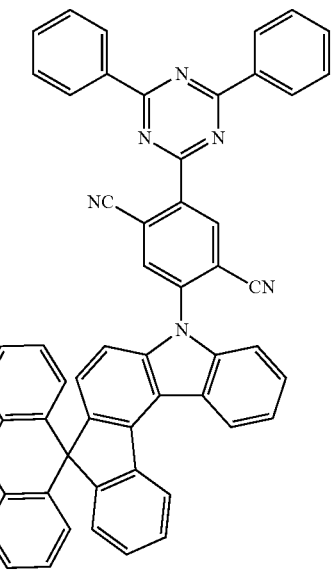
compound 3-5
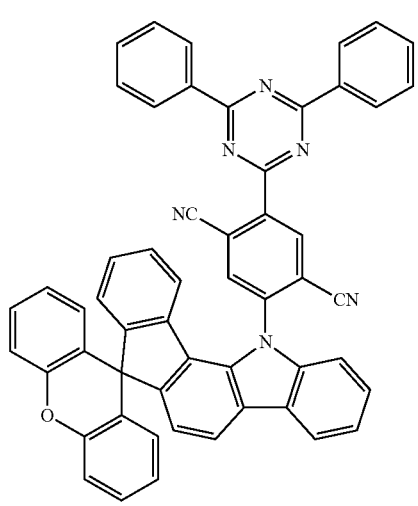
compound 3-3
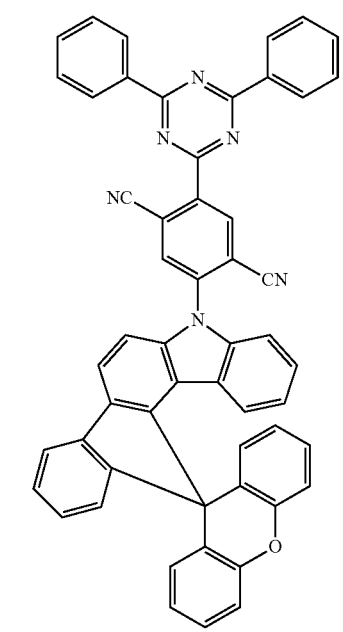
compound 3-6
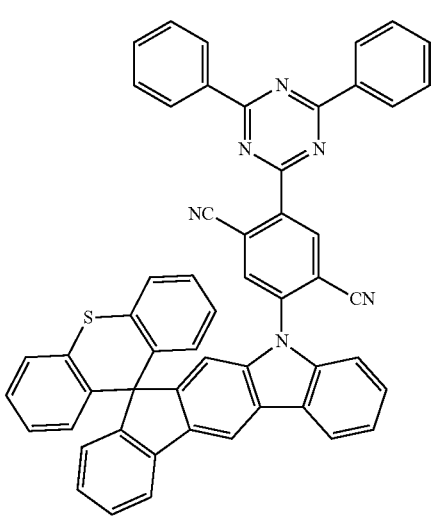

compound 3-7
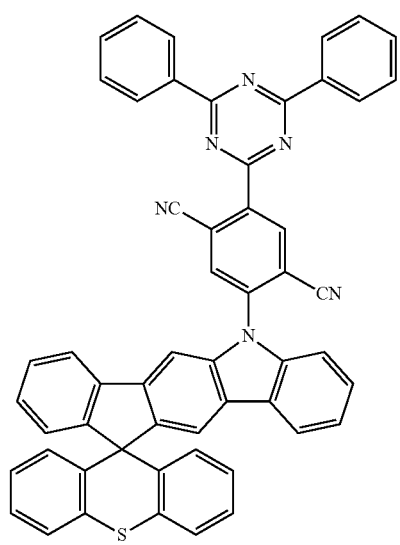
compound 3-9
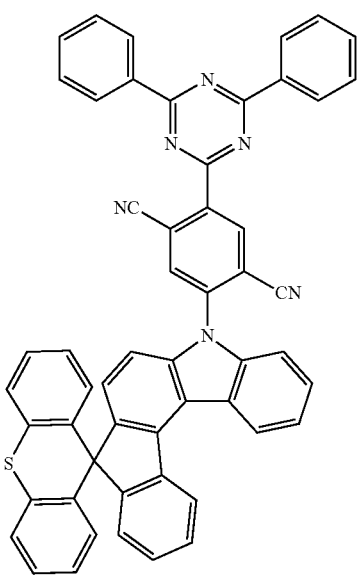
compound 3-10
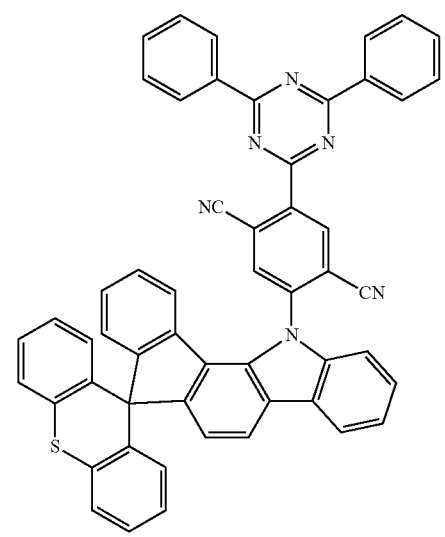
compound 3-8
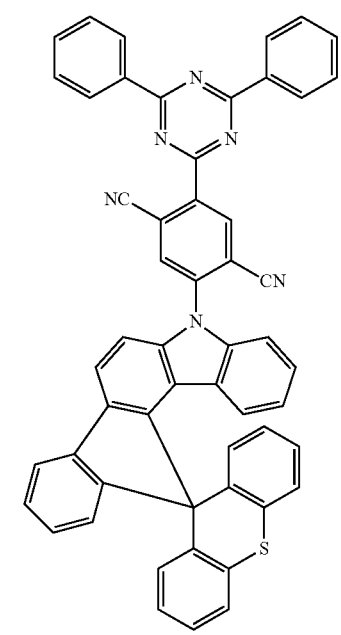
compound 4-1
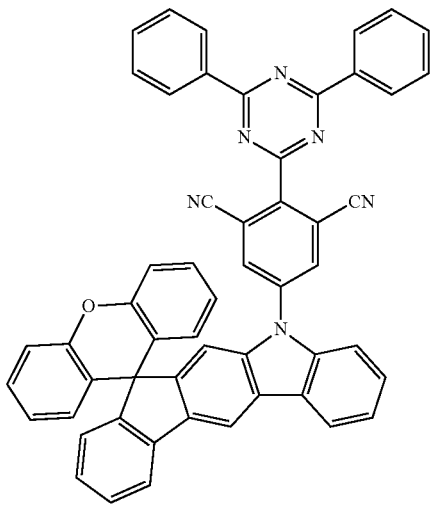

compound 4-2
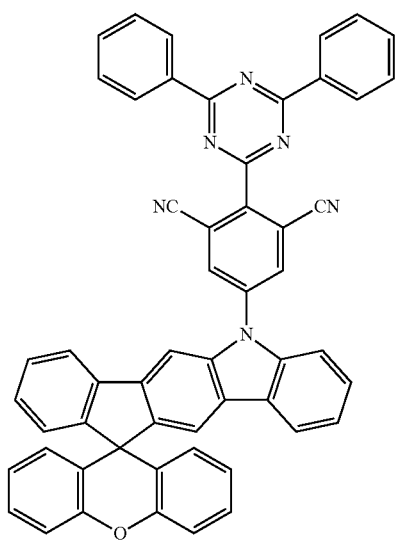
compound 4-4
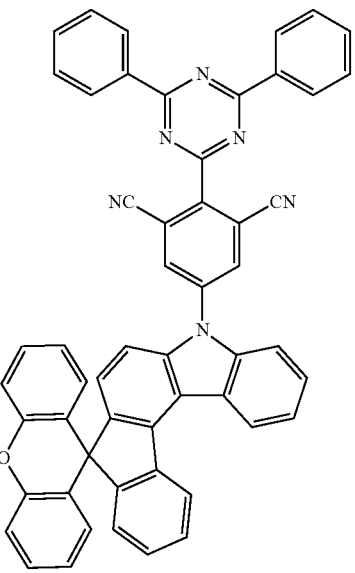
compound 4-5
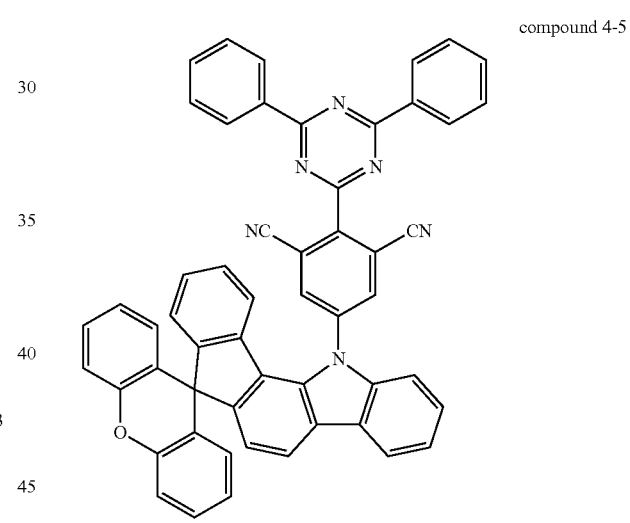
compound 4-3
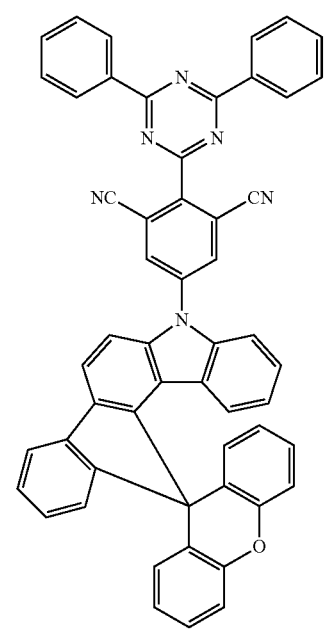
compound 4-6
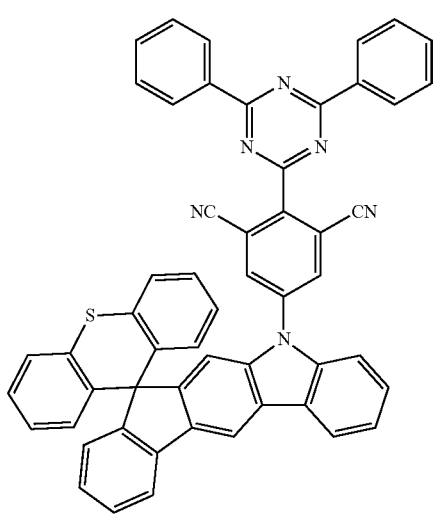

-continued
compound 4-7
compound 4-9
compound 4-8
compound 4-10
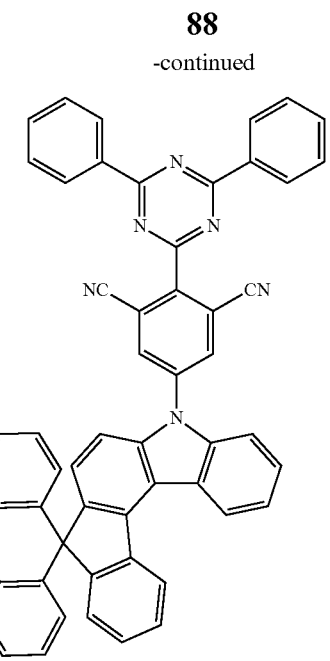
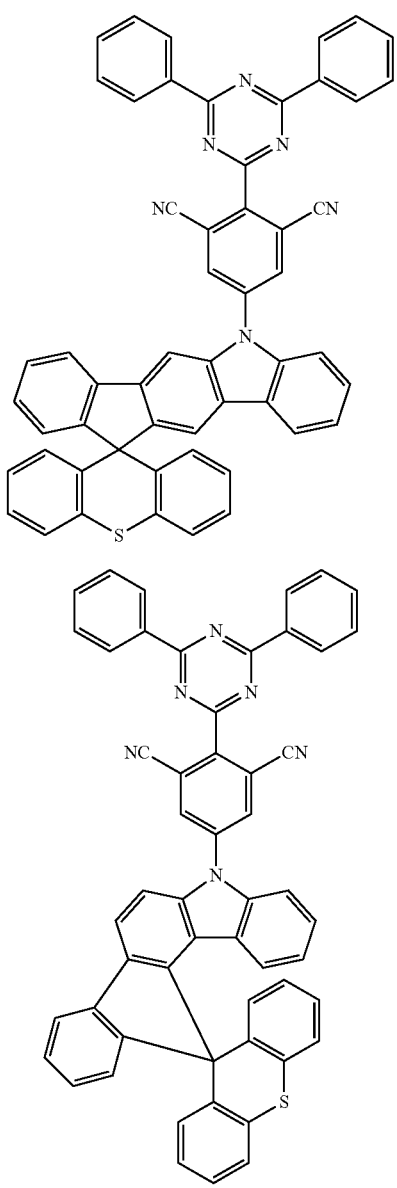
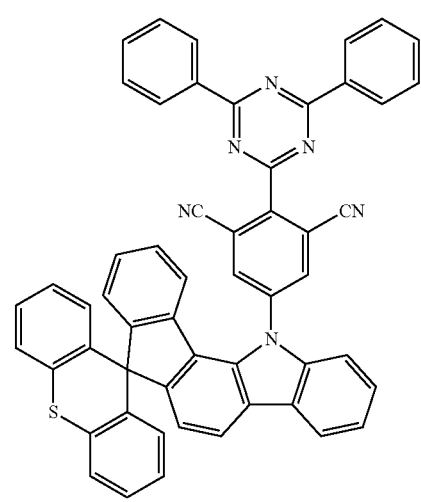
* * * * *